US009622911B2

(12) United States Patent
Rubinfeld et al.

(10) Patent No.: US 9,622,911 B2
(45) Date of Patent: Apr. 18, 2017

(54) OPHTHALMIC TREATMENT DEVICE, SYSTEM, AND METHOD OF USE

(71) Applicants: CXL Ophthalmics, LLC, Encinitas, CA (US); Brad Hartman, Renton, WA (US)

(72) Inventors: Roy S. Rubinfeld, Bethesda, MD (US); Sandy T. Feldman, Del Mar, CA (US); Kevin E. Daly, Encinitas, CA (US); Raymond A. Hartman, Carlsbad, CA (US)

(73) Assignee: CXL Ophthalmics, LLC, Encinitas, CA (US)

( * ) Notice: Subject to any disclaimer, the term of this patent is extended or adjusted under 35 U.S.C. 154(b) by 38 days.

(21) Appl. No.: 14/206,847

(22) Filed: Mar. 12, 2014

(65) Prior Publication Data

US 2014/0194957 A1     Jul. 10, 2014

Related U.S. Application Data

(63) Continuation-in-part of application No. 13/034,488, filed on Feb. 24, 2011, now abandoned.
(Continued)

(51) Int. Cl.
*A61B 18/20*     (2006.01)
*A61F 9/007*     (2006.01)
(Continued)

(52) U.S. Cl.
CPC ............ *A61F 9/0079* (2013.01); *A61F 9/008* (2013.01); *A61K 38/44* (2013.01);
(Continued)

(58) Field of Classification Search
CPC .............. A61F 9/008; A61F 9/013; A61F 2009/00865; A61F 2009/00872;
(Continued)

(56) References Cited

U.S. PATENT DOCUMENTS

| 4,676,790 A | 6/1987 | Kern |
| 4,863,627 A | 9/1989 | Davies et al. |

(Continued)

FOREIGN PATENT DOCUMENTS

| CA | 2319087 A1 | 8/1999 |
| CA | 2418306 A1 | 1/2002 |

(Continued)

OTHER PUBLICATIONS

International Search Report and Written Opinion for related PCT/US2014/024770 mailed on Aug. 6, 2014 in 17 pages.
(Continued)

*Primary Examiner* — Aaron Roane
(74) *Attorney, Agent, or Firm* — Procopio Cory Hargreaves & Savitch LLC

(57) ABSTRACT

Ophthalmic treatment systems and methods of using the systems are disclosed. The ophthalmic treatment systems include (a) a light source device; (b) at least one optical treatment head operatively coupled to the light source device, comprising a light source array, and providing at least one treatment light; and (c) a light control device, which (i) provides patterned or discontinuous treatment light projection onto an eye (e.g., the cornea and/or sclera of an eye); or (ii) adjusts intensity of part or all of the light source array, providing adjusted intensity treatment light projection onto an eye (e.g., the cornea and/or sclera of an eye). The at least one treatment light promotes corneal and/or scleral collagen cross-linking.

23 Claims, 18 Drawing Sheets

Related U.S. Application Data

(60) Provisional application No. 61/785,336, filed on Mar. 14, 2013, provisional application No. 61/388,362, filed on Sep. 30, 2010.

(51) Int. Cl.
*A61N 5/06* (2006.01)
*A61K 38/44* (2006.01)
*A61K 49/00* (2006.01)
A61F 9/013 (2006.01)
A61F 9/008 (2006.01)

(52) U.S. Cl.
CPC .......... *A61K 49/0015* (2013.01); *A61N 5/062* (2013.01); *A61F 9/013* (2013.01); *A61F 2009/00865* (2013.01); *A61F 2009/00872* (2013.01); *A61F 2009/00893* (2013.01)

(58) Field of Classification Search
CPC .......... A61F 2009/00893; A61K 38/44; A61K 49/0015; A61K 9/013; A61N 5/062
USPC ............................................................ 606/4
See application file for complete search history.

(56) References Cited

U.S. PATENT DOCUMENTS

| | | | |
|---|---|---|---|
| 5,368,590 A | 11/1994 | Itoh | |
| 5,639,481 A | 6/1997 | Kessler | |
| 5,849,291 A | 12/1998 | Kessler | |
| 6,043,237 A | 3/2000 | Meadows | |
| 6,099,521 A | 8/2000 | Shadduck | |
| 6,161,544 A | 12/2000 | DeVore et al. | |
| 6,162,210 A | 12/2000 | Shadduck | |
| 6,183,086 B1 | 2/2001 | Neubert | |
| 6,248,335 B1 | 6/2001 | Duan et al. | |
| 6,413,268 B1 | 7/2002 | Hartman | |
| 6,447,537 B1 | 9/2002 | Hartman | |
| 6,471,691 B1 | 10/2002 | Kobayashi | |
| 6,544,286 B1 | 4/2003 | Perez | |
| 6,783,539 B1 | 8/2004 | Timberlake | |
| 6,880,558 B2 | 4/2005 | Perez | |
| 7,015,252 B2 | 3/2006 | Fujii et al. | |
| 7,044,945 B2 | 5/2006 | Sand | |
| 7,073,510 B2 | 7/2006 | Redmond | |
| 7,077,839 B2 | 7/2006 | Hamblin | |
| 7,186,417 B1 | 3/2007 | Siegel | |
| 7,220,278 B2 | 5/2007 | Peyman | |
| 7,288,106 B2 | 10/2007 | Heacock | |
| 7,331,350 B2 | 2/2008 | Kochevar | |
| 7,479,136 B2 | 1/2009 | Dotson | |
| 7,498,156 B2 | 3/2009 | Goodrich | |
| 7,727,544 B2 | 6/2010 | Schwartz | |
| 7,744,590 B2 | 6/2010 | Eells | |
| 7,753,943 B2 | 7/2010 | Strong | |
| 7,943,590 B2 | 5/2011 | Flugelman | |
| 8,034,373 B2 | 10/2011 | Reynolds et al. | |
| 8,092,490 B2 | 1/2012 | Redmond et al. | |
| 8,100,530 B2 | 1/2012 | Zhou et al. | |
| 8,106,038 B2 | 1/2012 | Margaron et al. | |
| 8,177,778 B2 | 5/2012 | Muller et al. | |
| 8,215,314 B2 | 7/2012 | Chan et al. | |
| 8,238,993 B2 | 8/2012 | Maynard et al. | |
| 8,282,629 B2 | 10/2012 | Mrochen et al. | |
| 8,398,628 B2 | 3/2013 | Muller | |
| 8,574,277 B2 | 11/2013 | Muller et al. | |
| 8,580,789 B2 | 11/2013 | Krueger et al. | |
| 2001/0016731 A1 | 8/2001 | DeVore et al. | |
| 2002/0006394 A1 | 1/2002 | Redmond | |
| 2002/0013577 A1 | 1/2002 | Frey et al. | |
| 2002/0022606 A1 | 2/2002 | Kochevar | |
| 2002/0118338 A1* | 8/2002 | Kohayakawa | A61B 3/1233 351/206 |
| 2003/0083649 A1 | 5/2003 | Margaron | |
| 2003/0105521 A1 | 6/2003 | Perez | |
| 2003/0175259 A1 | 9/2003 | Karageozian et al. | |
| 2003/0208190 A1 | 11/2003 | Roberts et al. | |
| 2004/0137068 A1 | 7/2004 | Bhushan | |
| 2005/0070942 A1 | 3/2005 | Perez | |
| 2005/0090877 A1* | 4/2005 | Harth | A61N 5/0613 607/88 |
| 2005/0124982 A1 | 6/2005 | Perez | |
| 2005/0149006 A1 | 7/2005 | Peyman | |
| 2005/0152993 A1 | 7/2005 | De Oliveira | |
| 2005/0241653 A1 | 11/2005 | Heugten et al. | |
| 2005/0271590 A1 | 12/2005 | Schwartz et al. | |
| 2005/0283234 A1 | 12/2005 | Zhou et al. | |
| 2006/0074487 A1 | 4/2006 | Gilg | |
| 2006/0084951 A1 | 4/2006 | Heacock | |
| 2006/0106371 A1 | 5/2006 | Muhlhoff et al. | |
| 2006/0134170 A1 | 6/2006 | Griffith et al. | |
| 2006/0166879 A1 | 7/2006 | Bhushan et al. | |
| 2006/0172972 A1 | 8/2006 | Bhushan et al. | |
| 2006/0177430 A1 | 8/2006 | Bhushan et al. | |
| 2006/0206173 A1* | 9/2006 | Gertner | A61N 5/0616 607/88 |
| 2006/0235513 A1 | 10/2006 | Price, Jr. | |
| 2006/0268231 A1 | 11/2006 | Gil et al. | |
| 2006/0275278 A1 | 12/2006 | Choy et al. | |
| 2007/0021806 A1* | 1/2007 | Mercier | A61N 5/0616 607/88 |
| 2007/0088415 A1 | 4/2007 | Peyman | |
| 2007/0128174 A1 | 6/2007 | Kleinsek et al. | |
| 2007/0129286 A1 | 6/2007 | Zhang | |
| 2007/0135805 A1 | 6/2007 | Peyman | |
| 2007/0142828 A1 | 6/2007 | Peyman | |
| 2007/0167935 A1 | 7/2007 | Serdarevic | |
| 2007/0207116 A1 | 9/2007 | Brown | |
| 2007/0225778 A1 | 9/2007 | Heacock | |
| 2008/0009901 A1 | 1/2008 | Redmond | |
| 2008/0015660 A1 | 1/2008 | Herekar | |
| 2008/0039769 A1 | 2/2008 | Peyman | |
| 2008/0057023 A1 | 3/2008 | Chynn | |
| 2008/0097174 A1 | 4/2008 | Maynard et al. | |
| 2008/0114283 A1 | 5/2008 | Mattson | |
| 2008/0139671 A1 | 6/2008 | Herekar | |
| 2008/0161780 A1 | 7/2008 | Serdarevic | |
| 2008/0208177 A1 | 8/2008 | Mrochen et al. | |
| 2008/0246920 A1 | 10/2008 | Buczek et al. | |
| 2008/0269119 A1 | 10/2008 | Griffith et al. | |
| 2008/0269730 A1 | 10/2008 | Dotson | |
| 2008/0288063 A1 | 11/2008 | Price, Jr. | |
| 2009/0099557 A1 | 4/2009 | Sedarevic | |
| 2009/0105127 A1 | 4/2009 | Thompson | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0192437 A1 | 7/2009 | Soltz | |
| 2009/0275929 A1 | 11/2009 | Zickler | |
| 2010/0057059 A1 | 3/2010 | Makino | |
| 2010/0057060 A1 | 3/2010 | Herekar | |
| 2010/0069894 A1 | 3/2010 | Mrochen | |
| 2010/0087920 A1 | 4/2010 | Marmo | |
| 2010/0114109 A1 | 5/2010 | Peyman | |
| 2010/0173019 A1 | 7/2010 | Paik et al. | |
| 2010/0179622 A1* | 7/2010 | Wagenaar Cacciola | A61N 5/0614 607/94 |
| 2010/0189817 A1 | 7/2010 | Krueger et al. | |
| 2010/0210996 A1 | 8/2010 | Peyman | |
| 2010/0286156 A1 | 11/2010 | Pinelli | |
| 2010/0318017 A1 | 12/2010 | Lewis et al. | |
| 2011/0060129 A1 | 3/2011 | Akashi et al. | |
| 2011/0060267 A1 | 3/2011 | DeWoolfson et al. | |
| 2011/0081323 A1 | 4/2011 | Kleinsek et al. | |
| 2011/0086802 A1 | 4/2011 | Dewoolfson et al. | |
| 2011/0118654 A1 | 5/2011 | Muller et al. | |
| 2011/0125187 A1 | 5/2011 | Soltz et al. | |
| 2011/0149247 A1 | 6/2011 | Artsyukhovich | |
| 2011/0160710 A1 | 6/2011 | Frey et al. | |
| 2011/0237999 A1 | 9/2011 | Muller et al. | |
| 2011/0264082 A1 | 10/2011 | Mrochen et al. | |
| 2011/0282333 A1 | 11/2011 | Herekar et al. | |
| 2011/0288466 A1 | 11/2011 | Muller et al. | |

(56) References Cited

U.S. PATENT DOCUMENTS

| | | |
|---|---|---|
| 2011/0301524 A1 | 12/2011 | Bueler et al. |
| 2011/0306956 A1 | 12/2011 | Islam et al. |
| 2012/0059439 A1 | 3/2012 | Yoon |
| 2012/0065572 A1 | 3/2012 | Lewis et al. |
| 2012/0083772 A1 | 4/2012 | Rubinfeld et al. |
| 2012/0095455 A1 | 4/2012 | Rodmond et al. |
| 2012/0121567 A1 | 5/2012 | Troisi et al. |
| 2012/0203161 A1 | 8/2012 | Herekar |
| 2012/0215155 A1 | 8/2012 | Muller et al. |
| 2012/0238938 A1 | 9/2012 | Herekar et al. |
| 2012/0283531 A1 | 11/2012 | Maynard et al. |
| 2012/0283621 A1 | 11/2012 | Muller |
| 2012/0289886 A1 | 11/2012 | Muller et al. |
| 2012/0310083 A1 | 12/2012 | Friedman et al. |
| 2012/0310141 A1 | 12/2012 | Kornfield et al. |
| 2013/0060187 A1 | 3/2013 | Friedman et al. |
| 2013/0079759 A1 | 3/2013 | Dotson et al. |
| 2013/0085370 A1 | 4/2013 | Friedman et al. |
| 2013/0245536 A1 | 9/2013 | Friedman et al. |
| 2015/0126921 A1 | 5/2015 | Rubinfeld et al. |
| 2015/0174161 A1 | 6/2015 | Rubinfeld et al. |

FOREIGN PATENT DOCUMENTS

| | | |
|---|---|---|
| CA | 2473703 A1 | 7/2003 |
| CA | 2511217 A1 | 7/2004 |
| CA | 2515720 A1 | 9/2004 |
| CA | 2566961 A1 | 12/2005 |
| CA | 2576308 A1 | 2/2006 |
| CA | 2577025 A1 | 2/2006 |
| CA | 2700884 A1 | 2/2009 |
| DE | 10323422 A1 | 4/2004 |
| JP | S54-101440 A | 8/1979 |
| SU | 1803110 | 3/1993 |
| WO | 0182933 A2 | 11/2001 |
| WO | 03061518 A2 | 7/2003 |
| WO | 03068247 | 8/2003 |
| WO | 2004024035 A1 | 3/2004 |
| WO | 2005117987 A1 | 12/2005 |
| WO | 2007011874 A2 | 1/2007 |
| WO | 2007011875 A2 | 1/2007 |
| WO | 2007020673 | 2/2007 |
| WO | 2007026382 A1 | 3/2007 |
| WO | 2007035843 A2 | 3/2007 |
| WO | 2007082127 | 7/2007 |
| WO | 2008005059 | 1/2008 |
| WO | 2008055118 A2 | 5/2008 |
| WO | 2009001396 | 12/2008 |
| WO | 2009146151 A2 | 12/2009 |
| WO | 2010023705 | 3/2010 |
| WO | 2010093908 A2 | 8/2010 |
| WO | 2011011202 A1 | 2/2011 |
| WO | 2011019940 A2 | 2/2011 |
| WO | 2011041437 A1 | 4/2011 |
| WO | 2011050164 | 4/2011 |
| WO | 2011050164 A1 | 4/2011 |
| WO | 2011056477 | 5/2011 |
| WO | 2011109712 A2 | 9/2011 |
| WO | 2011152861 A2 | 12/2011 |
| WO | 2012035403 A1 | 3/2012 |
| WO | 2013148896 | 10/2013 |

OTHER PUBLICATIONS

International Search Report and Written Opinion PCT/US2011/033873 mailed Jan. 17, 2012 in 14 pages.
EMX Industries, Inc.; ColorMax HEX Color Sensors; Mar. 2010.
Wells et al. "Oxidative Stress in Developmental Origins of Disease: Teratogenesis, Neurodevelopmental Deficits, and Cancer." Toxicological Sciences. 108(1):4-18 (2009).
Uttara et al. "Oxidative Stress and Neurodegenerative Diseases: A Review of Upstream and Downstream Antioxidant Therapeutic Options." Current Neuropharmacology. 7:65-74 (2009).
Sukkar et al. "Oxidative stress and nutritional prevention in autoimmune rheumatic diseases." Autoimmunity Reviews. 3:199-206 (2004).
Bickers et al. "Oxidative Stress in the Pathogenesis of Skin Disease." The Society for Investigative Dermatology. pp. 2565-2575, 2006.
Gilgun-Sherki et al. "Oxidative stress induced-neurodegenerative diseases: the need for antioxidants that penetrate the blood brain barrier." Neuropharmacology. 40:959-975 (2001).
Oduntan et al. "A review of the role of oxidative stress in the pathogenesis of eye diseases." S Afr Optom. 70(4):191-199 (2011).
Kato et al. "Topography-Guided Conductive Keratoplasty: Treatment for Advanced Keratoconus." American Journal of Ophthalmology. 150(4):481-489 (Oct. 2010).
Kohnen et al. "Bewertung und Qualitatssicherung refraktivchirurgischer Eingriffe durch die DOG und den BVA (Evaluation and quality assurance of refractive surgery by the German Ophthalmological Society and the Professional Association of German Ophthalmologists)." Ophthalmologie. 108(9):869-882 (Sep. 2011). Available only in German.
Kullman. "Alternative Applications of the Femtosecond Laser in Ophthalmology." Seminars in Ophthalmology. 25 (5-6):256-264 (Nov. 2010).
Chuo et al. "Modern Corneal and Refractive Procedures." Expert Review of Ophthalmology. 6(2):247-266 (Apr. 2011).
Epstein."Refraktive Chirurgie." Therapeutische Umschau. Revue Therapeutique. 66(3):207-210 (Mar. 2009). English abstract.
International Search Report and Written Opinion for related international application No. PCT/US2013/033923, mailed Jul. 12, 2013, in 13 pages.
International Search Report and Written Opinion for related international application No. PCT/US2013/034185, mailed Jul. 11, 2013, in 12 pages.
Wollensak et al. "Wound Healing in the Rabbit Cornea After Corneal Collagen Cross-Linking With Riboflavin and UVA." Cornea. 26:600-605, 2007.
Wollensak et al. "Stress-strain measurements of human and porcine corneas after riboflavin-ultraviolet-A-induced cross-linking." J Cataract Refract Surg. 29:1780-1785, 2003.
Wollensak et al. "Riboflavin/Ultraviolet-A-induced Collagen Crosslinking for the Treatment of Keratoconus." Am J Ophthalmol. 135:620-627, 2003.
Bessonova et al. "A study of the stability of eye drops containing riboflavine (Russian)." XP002719481. Database accession No. EMB-1978057912. Abstract. Database EMBASE (Online). Elsevier Science Publishers, Amsterdam, NL, 1977.
Elstner et al. "Uptake and Biochemical Activity of Potassium Iodide in Isolated Rabbit Eyes." XP008167001. Ophtlalmologica. 191(2):122-126 (1985). English abstract provided.
Koltun et al. "Improving the production technology of vitamin-containing eye drops to ensure their microbiological purity." XP002719482. Database accession No. PREV199497454025. Abstract. Database Biosis (Online). Biosciences Information Service, Philadelphia, PA, US, 1993.
Rieger. "Anti-oxidative capacity of various artificial tear preparations." XP003014992. Graefe's Archive for Clinical Experimental Ophthalmology. 239:222-226 (2001).
Schmut et al. "Iodide protection from UVB irradiation-induced degradation of hyaluronate and against UVB-damage of human conjunctival fibroblasts." XP008166988. Graefe's Archive for Clinical Experimental Ophthalmology. 242 (4):279-283 (2004).
Shimmura et al. "Subthreshold UV Radiation-induced Peroxide Formation in Cultured Corneal Epithelial Cells: The Protective Effects of Lactoferrin." XP055098621. Experimental Eye Research. 63(5):519-526 (1996).
Ishimitsu et al. "The photochemical decomposition and hydroxylation of phenylalanine in the presence of riboflavin." XP008167014. Chemical and Pharmaceutical Bulletin, Pharmaceutical Society of Japan. 33(4):1552-1556 (1985).
Zhang et al. "Clinical effect of traditional Chinese herb combined with sodium iodide in treating corneal opacity." XP002719483. Database accession No. EMB-2007125131. Database EMBASE (Online). Elsevier Science Publishers, Amsterdam, NL, Feb. 2007.

(56) References Cited

OTHER PUBLICATIONS

Extended European Search Report mailed on Feb. 10, 2014 for related EP Patent Application No. 11831060 in 15 pages.
Cho et al. "Reactive Oxygen Species-Induced Apoptosis and Necrosis in Bovine Corneal Endothelial Cells." Investigative Ophthalmology & Visual Science. 40(5):911-919, Apr. 1999.
Fujimori. "Cross-linking and fluorescence changes of collagen by glycation and oxidation." Biochimica et Blophysica Acta. 998:105-110, 1989.
Hull et al. "Hydrogen Peroxide-Mediated Corneal Endothelial Damage." Investigative Ophthalmology & Visual Science. 25:1246-1253, 1984.
Iseli et al. "Efficacy and Safety of Blue-light Scleral Cross-linking." International Congress of Corneal Cross-Linking, Dec. 7-8, 2007; Zurich, Switzerland. pp. S752-S755.
Khadem et al. "Photodynamic Biologic Tissue Glue." Cornea. 13(5):406-410, 1994.
Kohlhaas et al. "Biomechanical evidence of the distribution of cross-links in corneas treated with riboflavin and ultraviolet a light." J Cataract Refract Surg. 32:279-283, Feb. 2006.
Krueger et al. "Rapid vs Standard Collagen CXL with Equivalent Energy Dosing." Third International Congress of Corneal Crosslinking. Dec. 7-8, 2007; Zurich, Switzerland, in 25 pages.
Sato et al. "The Primary Cytotoxicity in Ultraviolet-A-Irradiated Riboflavin Solution is Derived from Hydrogen Peroxide." The Society for Investigative Dermatology, Inc. 105(4):608-612, Oct. 1995.
Seiler et al. "Corneal Cross-Linking-Induced Stromal Demarcation Line." Clinical Science. 25(9):1057-1059, Oct. 2006.
Spoerl et al. "Increased resistance of crosslinked cornea against enzymatic digestion." Current Eye Research. 29 (1):35-40, 2004.
Spoerl et al. "Induction of Cross-links in Corneal Tissue." Exp. Eye Res. 66:97-103, 1998.
Spoerl et al. "Safety of UVA-Riboflavin Cross-Linking of the Cornea." Cornea. 26(4):385-389, May 2007.
Spoerl et al. "Thermomechanical Behavior of Collagen-Cross-Linked Porcine Cornea." Ophthalmologica. 218:136-140, 2004.
Wollensak et al. "Collagen Fiber Diameter in the Rabbit Cornea After Collagen Crosslinking by Riboflavin/UVA." Cornea. 23(5):503-507, Jul. 2004.
Wollensak et al. "Corneal Endothelial Cytotoxicity of Riboflavin/UVA Treatment in vitro." Ophthalmic Res. 35:324-328, 2003.
Wollensak et al. "Endothelial cell damage after riboflavin-ultraviolet-A treatment in the rabbit." J Cataract Refract Surg. 29:1786-1790, 2003.
Wollensak et al. "Keratocyte Apoptosis After Corneal Collagen Cross-linking Using Riboflavin/UVA Treatment." Cornea. 23(1):43-49, Jan. 2004.
Wollensak et al. "Keratocyte cytotoxicity of riboflavin/UVA treatment in vitro." Eye. 2004, in 5 pages.
Wollensak et al. "Long-term biomechanical properties of rabbis cornea after photodynamic collagen crosslinking." Acta Ophthalmologica. 87:48-51, 2009.
Wollensak et al., "Cross-linking of scleral collagen in the rabbit using riboflavin and UVA", ACTA Ophthalmologica Scandinavica, 2005, vol. 83, pp. 477-482.
International Search Report and Written Opinion for related international application No. PCT/US2013/034467 mailed on Jul. 26, 2013 in 12 pages.
Agbor, et al. "Effect of Iodine Supplementation on Antioxidant Status of Normal and Alloxan Monohydrate in Toxicated Rats", International Journal of Pharmacology, 7 (6): pp. 726-731, 2011, Asian Network for Scientific Information.
Rieger, et al. "The Effect of Iodide Iontophoresis on the Antioxidative Capacity of the Tear Fluid" Graefe's Archive for Clinical Experimental Ophthalmology. 248:1639-1646 (2010).
Rieger, "Anti-oxidative Capacity of Various Artificial Tear Preparations", Graefe's Arch. Clin. Exp. Opthalmol., 2001, vol. 239, pp. 222-226.
El-Raggal, "Riboflavin-Ultraviolet a Corneal Cross linking for Keratoconus", Middle East African Journal of Opthalmology, Oct.-Dec. 2009; 16(4): 256-259, 8 pages.
Supplementary European Search Report for EP 13767439.6 mailed on Sep. 15, 2015 in 6 pages.
Rose, R. C. et al.: "Ocular oxidants and antioxidant protection", Experimental Biology and Medicine, vol. 217, No. 4, 1998, pp. 397-407.
Ibusuki et al: "Photochemically Cross-Linked Collagen Gels as Three-Dimensional Scaffolds for Tissue Engineering", Tissue Engineering, vol. 13, No. 8, Aug. 14, 2007, pp. 1995-2001.
Horwath-Winter J, et al: "Iodide iontophoresis as a treatment for dry eye syndrome", The British Journal of Ophthalmology, Jan. 2005, pp. 40-44, vol. 89, No. 1.
Singh et al: "Clinical Evaluation of Sodium Iodide in the Treatement of Various Types of Cataracts", Journal of the Indian Medical Association, 1983, pp. 119-121, vol. 81, No. 7-8.
Winkler et al: "Effect of Iodide on Total Antioxidant Status of Human Serum", Cell Biochemistry and Function, Jun. 2000, pp. 143-146, vol. 18, No. 2.
Partial supplementary European Search Report for EP 13768403.1 mailed on Oct. 23, 2015 in 10 pages.
J. Wernli, S. Schumacher, E. Spoerl, and M. Mrochen, The efficacy of corneal cross-linking shows a sudden decrease with very high intensity UV light and short treatment time, Investigative Ophthalmology and Visual Science, vol. 54, No. 2, pp. 1176-1180, Feb. 2013.
R. R Krueger, E Spoerl, and S. Herekar, "Rapid vs standard collagen CXL with equivalent energy dosing," in Proceedings of the 3rd International Congress of Corneal Collagen Cross-Linking, Zurich, Switzerland, Dec. 2007.
Pavel Kamaev, et al., Photochemical Kinetics of Corneal Cross-Linking with Riboflavin, Investigative Ophthalmology & Visual Science, Apr. 2012, vol. 53, No. 4.
Extended European Search Report for European patent application No. 14775693.6 mailed on Oct. 19, 2016 in 8 pages.

\* cited by examiner

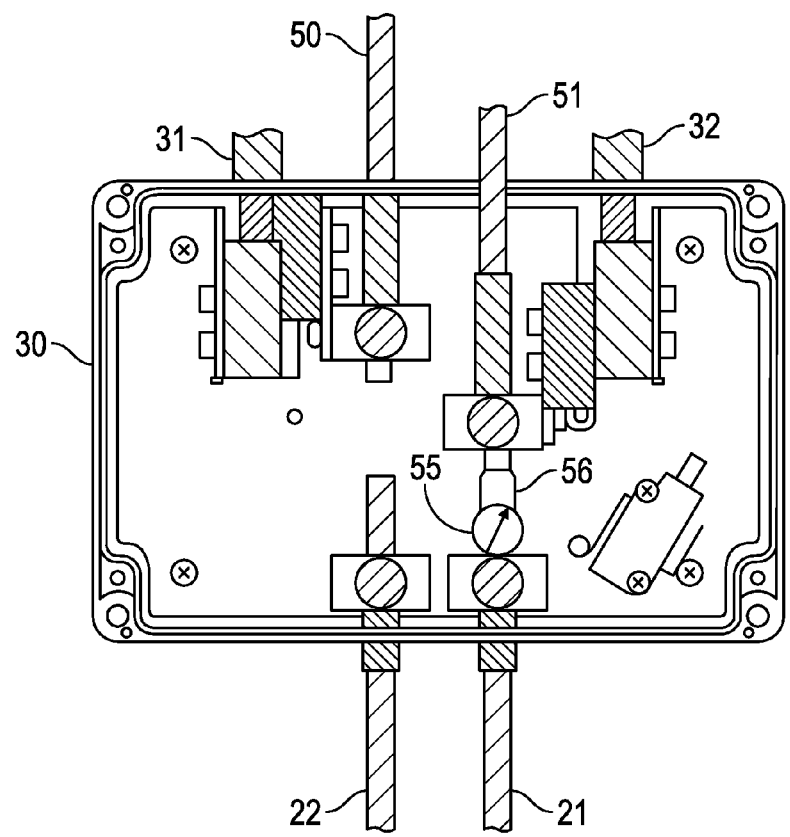
FIG. 7
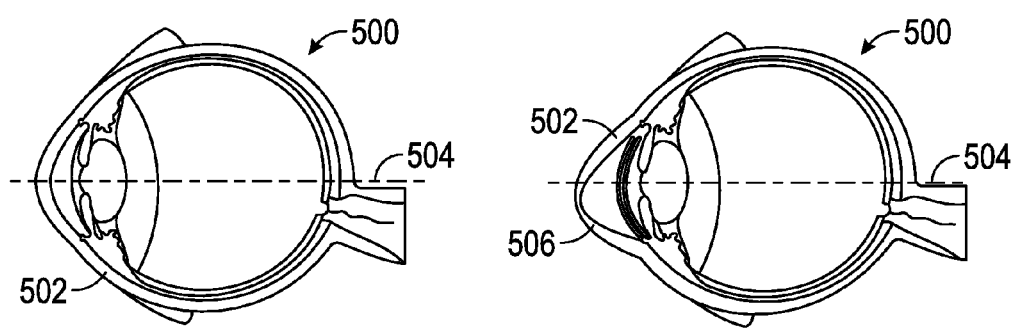
FIG. 8A  FIG. 8B

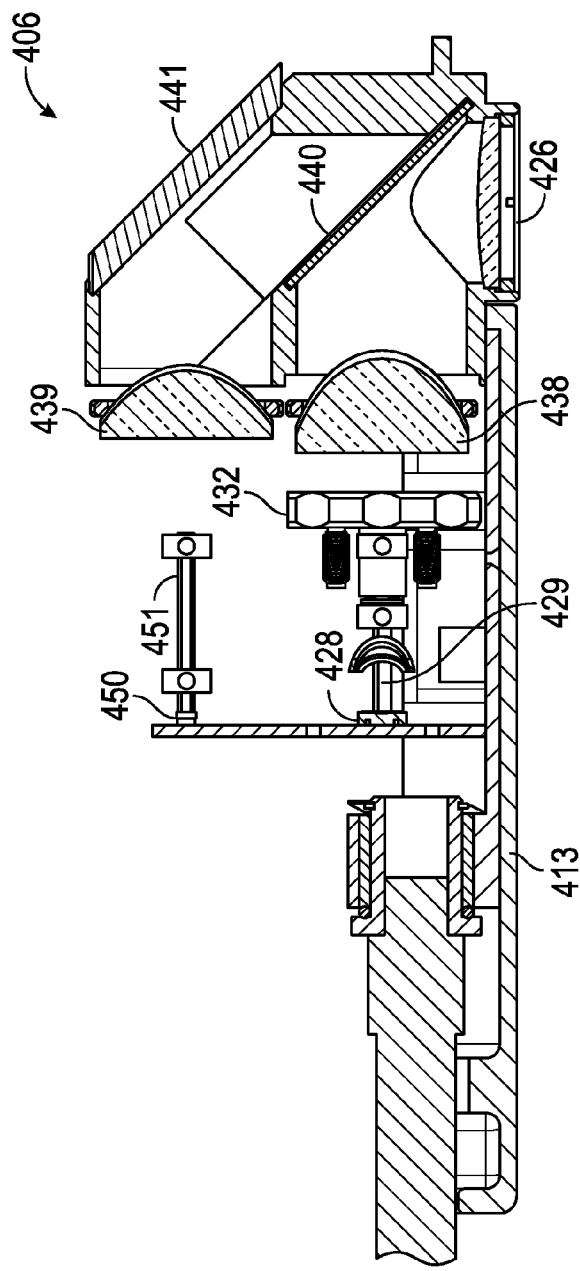
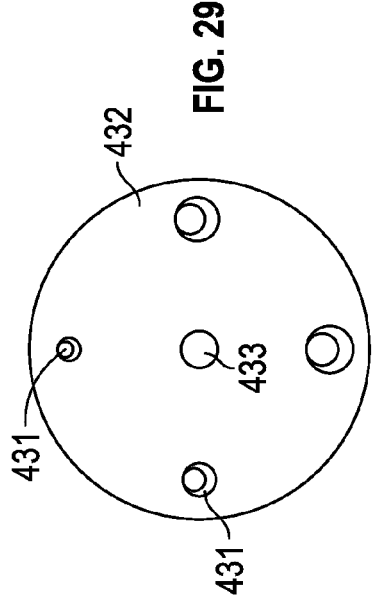
FIG. 28
FIG. 29

OPHTHALMIC TREATMENT DEVICE, SYSTEM, AND METHOD OF USE

This application claims priority from provisional patent application No. 61/785,336 filed on Mar. 14, 2013, and is a Continuation in part of application Ser. No. 13/034,488 filed on Feb. 2, 2011, which claims the benefit of provisional patent application No. 61,388,362 filed on Sep. 30, 2010, and the contents of each of the aforementioned applications are incorporated herein by reference in their entirety.

BACKGROUND OF THE DISCLOSURE

Corneas and scleras derive their structural strength, shape and integrity from collagen. The strength of the intertwined collagen strands is a function of covalent cross-links established between and within collagen strands and between collagen and glycoproteins in the matrix. In structurally robust corneas and scleras, an enzyme called lysyl oxidase performs the collagen cross-linking function in a process called oxidative deamination using molecular oxygen present in the tissue. The biomechanical strength of corneal and scleral collagen can be reduced by a number of conditions including iatrogenic effect from surgical intervention, prosthesis, or medications, or the cause of corneal or scleral weakness can be congenital, idiopathic or due to microbial causes or trauma. In these cases of corneal or scleral weakness, interventional strategies to strengthen the collagen or to reduce infections are often employed.

SUMMARY OF THE DISCLOSURE

Disclosed herein, in certain embodiments, are ophthalmic treatment systems, comprising (a) a light source device; (b) at least one optical treatment head operatively coupled to the light source device, comprising a light source array, and providing at least one treatment light; and (c) a light control device, which (i) provides patterned or discontinuous treatment light projection onto an eye (e.g., the cornea and/or sclera of an eye); and/or (ii) adjusts intensity of part or all of the light source array, providing adjusted intensity treatment light projection onto an eye (e.g., the cornea and/or sclera of an eye). In some embodiments, the light control device directs the at least one treatment light. In some embodiments, the light source array device comprises a light source or a plurality of light sources. In some embodiments, the system further comprises an optical projection device configured to direct the at least one treatment light onto an eye (e.g., the cornea and/or sclera of an eye). In some embodiments, the system further comprises an optical projection device configured to direct the at least one treatment light onto a portion of an eye (e.g., the cornea and/or sclera of an eye). In some embodiments, the light control device applies the at least one treatment light to an eye (e.g., the cornea and/or sclera of an eye) in a predetermined pattern. In some embodiments, the light control device applies the at least one treatment light to an eye (e.g., the cornea and/or sclera of an eye) in a plurality of predetermined patterns. In some embodiments, the light control device independently blocks or unblocks part of the light source array and independently adjusts the intensity of part of the light source array such that the array provides a plurality of treatment lights having a plurality of intensities. In some embodiments, the light source comprises one or more laser diodes or LEDs. In some embodiments, a controller controls the light source to provide discontinuous treatment light projection onto the eye at a predetermined treatment light exposure period between 1 second and 10 minutes. In some embodiments, each treatment light exposure period of the discontinuous treatment is between around 5 seconds and 25 seconds. In some embodiments, the treatment light exposure period is around 15 seconds. In some embodiments, the treatment light is in a frequency range from 350 to 400 nm. In some embodiments, the at least one treatment light promotes collagen cross-linking. In some embodiments, the at least one treatment light promotes corneal or scleral collagen cross-linking. In some embodiments, corneal or scleral collagen cross-linking strengthens the cornea and/or sclera, or reduces or treats infections in the eye. In some embodiments, the light control device comprises a light modulating device which partially or entirely blocks or unblocks the part or all of the light source array, providing the discontinuous treatment light projection on the eye (e.g., the cornea and/or sclera of an eye). In some embodiments, the light modulating device is a shutter or filter. In some embodiments, the light modulating device is manually operated. In some embodiments, the light modulating device is operatively connected to a controller which controls movement of the light modulating device. In some embodiments, the controller comprises a microprocessor for controlling the blocking or unblocking of the part or all of the light source array. In some embodiments, the controller comprises an input for operator selection of parameters and duration for the discontinuous light projection on the cornea and/or sclera. In some embodiments, the light control device comprises an intensity control device which adjusts intensity of part or all of the light source array, providing the adjusted intensity treatment light projection onto an eye (e.g., the cornea and/or sclera of an eye). In some embodiments, the intensity control device is manually operated. In some embodiments, the intensity control device comprises a microprocessor to adjust intensity of part or all of the light source array. In some embodiments, the intensity control device comprises an input for operator adjustment of light intensity. In some embodiments, the system further comprises a pattern control device which provides patterned treatment light projection onto an eye (e.g., the cornea and/or sclera of an eye). In some embodiments, the pattern control unit is part of a light mask. In some embodiments, the pattern control unit comprises at least one filter or shutter. In some embodiments, the pattern control unit comprises a microprocessor which controls movement of the pattern control unit. In some embodiments, the pattern control device comprises an input for operator control of the patterned treatment light projection. In some embodiments, the pattern control unit moves. In some embodiments, the pattern control unit rotates. In some embodiments, the system further comprises a control unit which adjusts movement of the pattern control device. In some embodiments, the system further comprises a sensor device. In some embodiments, the blocking and unblocking of part or all of the light source array, or the adjusting of the intensity of part or all of the light source array, is controlled or adjusted according to data collected from the sensor device. In some embodiments, the sensor device is an optical collection device. In some embodiments, the optical collection device collects photoluminescent emissions from an eye (e.g., the cornea and/or sclera of an eye). In some embodiments, the sensor device comprises a photoluminescent monitoring module which measures the intensity of photoluminescent emissions from an eye (e.g., the cornea and/or sclera of an eye). In some embodiments, the photoluminescent monitoring module comprises a first band pass filter connected to the output of the optical collection device, the first band pass filter having a center wavelength corresponding to the peak of fluorescence emission of the photosensitizer, and a first sensor which receives the output of the first band pass filter output to produce a first output signal dependent on the detected fluorescence emission from the eye (e.g., the cornea and/or sclera of an eye). In some embodiments, the photoluminescent monitoring module further comprises a second band pass filter connected to the output of the optical collection device in parallel with the first band pass filter, the second band pass filter having a center wavelength corresponding to the peak of phosphorescence of an excited state of the photosensitizer, a second sensor which receives the output of the second band pass filter to produce a second output signal dependent on the intensity of detected phosphorescence from the eye (e.g., the cornea and/or sclera of an eye). In some embodiments, the system further comprises a processor which receives first and second output signals and which is configured to process the first output signal and produce an output signal which varies in response to variations in a concentration of the photosensitizer in an eye. In some embodiments, the sensor device comprises an environmental monitoring module which monitors concentrations of photosensitizer, oxygen, or both in the eye. In some embodiments, the system further comprises a fixation light upon which an eye is focused, providing a static treatment area. In some embodiments, the system further comprises a periodical visual or audio cue. In some embodiments, the system further comprises an auxiliary light source configured to be turned on if the at least one treatment light is discontinued or adjusted. In some embodiments, the optical treatment head is positioned at a working distance from the eye sufficient to allow access to the eye (e.g., the cornea and/or sclera of an eye). In some embodiments, the working distance is at least two inches. In some embodiments, the working distance is about three inches. In some embodiments, the working distance is from about three inches to about six inches. In some embodiments, the light source device comprises at least one single-wavelength light source. In some embodiments, the light source device comprises a plurality of single-wavelength light sources. In some embodiments, the at least one single-wavelength light source is an LED or a laser diode. In some embodiments, the light source device comprises a multi-wavelength light source. In some embodiments, the light source device further comprises a wavelength control device operatively coupled to the multi-wavelength light source. In some embodiments, the wavelength control device allows transmission of treatment light of at least one predetermined wavelength band and blocks transmission of light outside of the predetermined wavelength band. In some embodiments, the multi-wavelength light source comprises a short-arc lamp. In some embodiments, the short-arc lamp is a mercury lamp, a mercury halide lamp, or a xenon lamp. In some embodiments, the multi-wavelength light source further comprises a beam isolator configured to direct treatment light of wavelength ranging from about 330 to about 380 nm to the wavelength control device. In some embodiments, the beam isolator is configured to direct both UVA and blue light to the wavelength control device. In some embodiments, beam isolator comprises a UVA and blue light reflective dichroic mirror. In some embodiments, the wavelength control device allows selective transmission of treatment light of at least two different predetermined wavelength bands. In some embodiments, the wavelength control device comprises at least first and second filters and a controller configured to alternate between the first and second filters. In some embodiments, the first filter is a UVA filter and the second filter is a blue light filter. In some embodiments, the UVA filter has about 10 nm bandwidth at 365 nm and the blue light filter has about 10 nm bandwidth at 405 nm. In some embodiments, the system further comprises a support stand, an adjustable mounting assembly on a support stand, the optical treatment head supported on the mounting assembly, wherein the mounting assembly is configured for X and Y directional adjustment of the position of the optical treatment head relative to the eye. In some embodiments, the adjustable mounting assembly comprises a goose neck mounting arm connected to the optical treatment head. In some embodiments, the mounting assembly comprises an articulated arm having a first end mounted for vertical sliding adjustment on the support stand and a second end supporting the optical treatment head. In some embodiments, the mounting assembly includes a swivel joint configured for adjustment of an angle of the light beam directed from the optical treatment head to the eye (e.g., the cornea and/or sclera of an eye). In some embodiments, the system comprises a first and a second optical treatment head, each having a light source array. In some embodiments, the first and the second optical treatment heads each independently project treatment light onto the left eye (e.g., the cornea and/or sclera of the left eye) or the right eye (e.g., the cornea and/or sclera of the right eye). In some embodiments, the system comprises a mounting assembly having a first portion and second portion each independently associated with one of the two optical treatment heads. In some embodiments, the mounting assembly comprises an articulated arm assembly having a first portion slidably associated with the support stand, the first portion and second portions of the mounting assembly being pivotally connected to the first portion of the articulation arm assembly. In some embodiments, one of the end portions is articulated. In some embodiments, the mounting assembly further comprises first and second swivel joints between the first and second optical treatment heads, respectively. In some embodiments, the system further comprises locking devices configured for releasable locking the first optical treatment head and the second optical treatment head, at a selected X, Y and Z adjusted position relative to a respective eye of a patient. In some embodiments, the system comprises a first and a second optical treatment head each including projection optics and configured to project respective treatment light onto the right and left eyes (e.g., the cornea and/or sclera of the left and right eyes) at a predetermined working distance from the optical heads. In some embodiments, the first optical treatment head and second optical treatment head are adjustably mounted for at least x and y direction adjustment of the position of the optical treatment head relative to the respective eyes. In some embodiments, the system further comprises an intensity adjustment module configured to independently adjust intensity of part or all of the light source array projected by the first optical treatment head and second optical treatment head. In some embodiments, the system further comprises an adjustable mounting assembly configured for adjusting the separation between the first and second optical treatment heads and the distance of each optical treatment head from the respective eyes. In some embodiments, the adjustable mounting assembly includes independent swivel joints configured for adjusting an angle of each optical head relative to the respective eye. In some embodiments, the system further comprises an adjustment mechanism configured for varying distance of the optical treatment head from the eye. In some embodiments, the light source device further comprises an aesthetic light which is visible to an observer, and optionally not visible to a patient. In some embodiments, the light source device further comprises a plurality of aesthetic lights which are visible to an observer, and optionally not visible to a patient. In some embodiments, the aesthetic lights are activated when the light source device is activated and providing the at least one treatment light.

Described herein, in certain embodiments, are methods of producing a treatment light for use in phototherapy treatment of an eye (e.g., the cornea and/or sclera of an eye), comprising (a) directing light from a multi-wavelength light source to a wavelength control device; (b) isolating and directing treatment light of at least one predetermined wavelength band to at least one optical treatment head; and (c) projecting a light beam from the optical treatment head and focusing the beam to produce a light spot of predetermined size and shape on the eye (e.g., the cornea and/or sclera of the eye) at a predetermined working distance from the optical treatment head, whereby the optical treatment head is positioned at a distance from the eye sufficient to allow access to the eye (e.g., the cornea and/or sclera of the eye). In some embodiments, the method comprises splitting the at least one treatment light along separate first and second optical paths, and directing the separated treatment lights to a first optical treatment head and a second optical treatment head for simultaneous treatment of right and left eyes (e.g., the cornea and/or sclera of the right and left eyes). In some embodiments, the method further comprises adjusting a distance between the first optical treatment head and the second optical treatment head based on a distance between the right and left eyes. In some embodiments, the method further comprises independently adjusting the first optical treatment head and the second optical treatment head to adjust an angle at which the at least one treatment light is projected on the respective eye (e.g., the cornea and/or sclera of the eye). In some embodiments, the method further comprises independently adjusting the intensity of the at least one treatment light applied to the respective eye (e.g., the cornea and/or sclera of the eye). In some embodiments, the method further comprises blocking and unblocking the at least one treatment light beam at predetermined time intervals to provide discontinuous light projection on the cornea and/or sclera. In some embodiments, the method further comprises contacting the eye (e.g., the cornea and/or sclera of the eye) with a photosensitizer. In some embodiments, the photosensitizer is riboflavin, rose Bengal, other photosensitizers, or derivatives thereof. In some embodiments, the method further comprises monitoring the level of photoluminescent emissions from the eye (e.g., the cornea and/or sclera of the eye) during treatment and determining approximate photosensitizer concentration in the eye (e.g., the cornea and/or sclera of the eye) is based on the level of photoluminescent emissions. In some embodiments, the method further comprises controlling an aperture in the optical treatment head, whereby intensity of the at least one treatment light and the size of the light spot is variable.

BRIEF DESCRIPTION OF THE DRAWINGS

FIG. 7 is a layout view of the intensity adjustment mechanism for the excitation light guides;

FIG. 8A is a cross-sectional view through an eye with a normal cornea and/or sclera;

FIG. 8B is a cross-sectional view through an eye affected by keratoconus offset from the central axis of the eye;

FIG. 28 is a cross-sectional view on the lines 28-28 of FIG. 27;

FIG. 29 is a front plan view of the reticle wheel of FIG. 28; and

Figure 1:
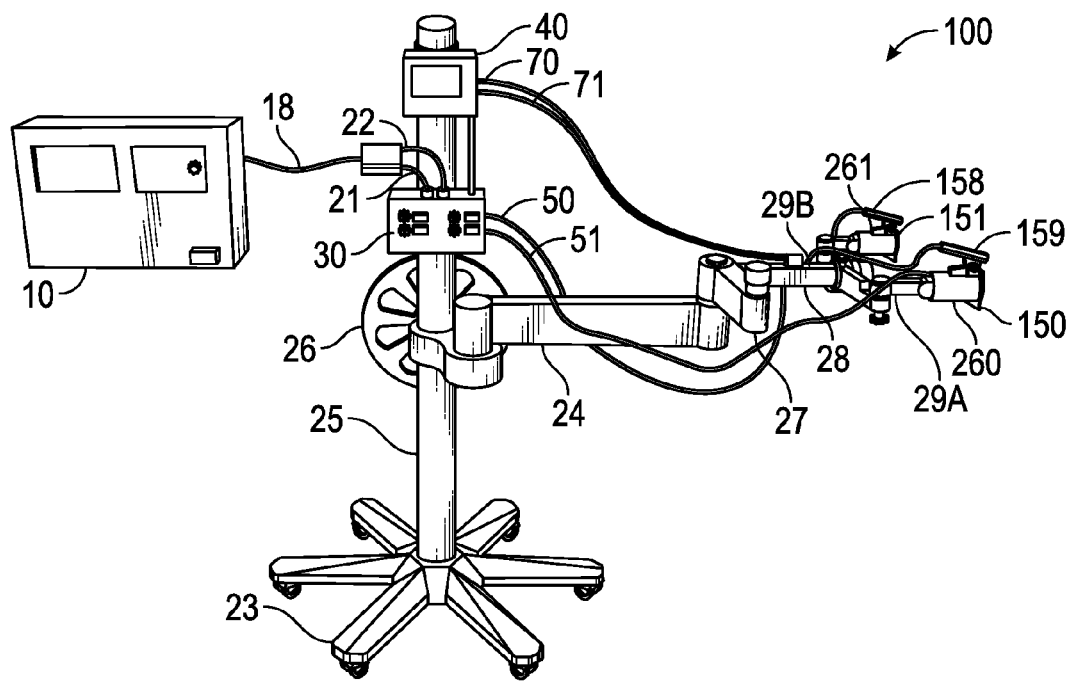
FIG. 1 is a perspective view of an embodiment of a bilateral treatment system or photochemical treatment and monitoring system.

It should be understood that the drawings are not necessarily to scale and that the disclosed embodiments are sometimes illustrated diagrammatically and in partial views. In certain instances, details which are not necessary for an understanding of the disclosed apparatus or method which render other details difficult to perceive are omitted. It should be understood, of course, that this disclosure is not limited to the particular embodiments illustrated herein.

DETAILED DESCRIPTIONS

The present disclosure relates generally to ophthalmic device, system, and method for treating a cornea or sclera of an eye, in particular for treating a cornea or sclera weakened by various medical or surgical conditions, for reducing infection, or for imparting refractive changes to the entire or selected portions of the eye (e.g., the cornea or sclera) to correct or otherwise improve vision.

Corneal and/or scleral collagen cross-linking shortens the length and increases the diameter of corneal and/or scleral collagen. In some cases, corneal and/or scleral collagen cross-linking is beneficial in corneas and/or scleras that would benefit from refractive correction to improve vision. Corneal and/or scleral tissue segments can be cross-linked selectively so as to control and customize refractive changes to meet the individual vision correction needs of the patient.

One method of cross-linking corneal and/or scleral collagen or strengthening collagen to impart refractive change and improve vision is photochemical cross-linking. The method of photochemical cross-linking uses a photosensitizer, usually riboflavin monophosphate, and UVA light to promote the cross-linking of the collagen fibrils. Photochemical cross-linking of the cornea has been demonstrated to slow, stop, or reverse the progression of compromised collagen in patients with keratoconus and ectasia.

Disclosed herein, in certain embodiments, are ophthalmic treatment systems, comprising a light source device or light source array and a light control device, which blocks or unblocks the part or all of the light source array for predetermined intervals, and which may be configured to provide patterned or discontinuous treatment light projection onto an eye (e.g., the cornea and/or sclera of an eye); or which may adjust intensity of part or all of the light source array, providing adjusted intensity treatment light projection onto an eye (e.g., the cornea and/or sclera of an eye). In some embodiments, the light source may comprise a plurality of light sources.

As used herein, "light source array" means an ordered or disordered arrangement of at least one light source. In some embodiments, the light source array comprises one light source. In some embodiments, the light source array comprises a plurality of light sources. In some embodiments, the plurality of light sources are in an ordered arrangement. In some embodiments, the plurality of light sources are in a disordered arrangement.

Discontinuous/Adjustable/Patterned Light Projection

In some embodiments of the ophthalmic treatment systems disclosed herein, the light control device includes a manual or microprocessor-controlled mechanical light modulation device (e.g., a shutter or filter) which is placed in the path of the light beam, at the appropriate position, providing discontinuous projection of treatment light on the eye (e.g., the cornea and/or sclera). In some embodiments, the on/off times for the discontinuous projection of treatment light on the eye (e.g., the cornea and/or sclera) is dependent on the concentrations of the photosensitizer (both excited state and ground state) and/or the partial pressure of the oxygen in the eye (e.g., the cornea and/or sclera). In some embodiments, the on/off times for the discontinuous projection of treatment light on the eye (e.g., the cornea and/or sclera) is controlled manually. In another embodiment, the on/off times for the discontinuous projection of treatment light on the eye (e.g., the cornea and/or sclera) is controlled automatically based on input by the physician at a control unit to determine overall treatment time and duration of on/off cycles. In another embodiment, the on/off times for the discontinuous projection of treatment light on the eye (e.g., the cornea and/or sclera) is microprocessor-controlled on the basis of the ratio of riboflavin phosphorescence at 605 nm in relation to riboflavin fluorescence at 525 nm detected from a measurement/sensor device in each treatment head. As the ratio of triplet state riboflavin phosphorescence of 605 nm/525 nm fluorescence drops, the microprocessor controls on/off times in accordance with the riboflavin concentration and/or oxygen partial pressure. When the light is shuttered or filtered, the oxygen consumption by the riboflavin triplets stops and the eye (e.g., the cornea and/or sclera) reoxygenates from the tear film or from oxygenated ophthalmic solutions applied to the eye (e.g., the cornea and/or sclera). In another embodiment, the discontinuous/adjustable/patterned light projection device is provided separately for use in other commercially available UVA/blue light emitting devices.

In some embodiments of the ophthalmic treatment systems, the light control device includes a manual or microprocessor-controlled optical shutter (e.g. a UVA/blue light filter) which is placed in the path of the light beam, at the appropriate position, so as to provide discontinuous projection of treatment light on the eye (e.g., the cornea and/or sclera). In some embodiments, the filtered/unfiltered times for the discontinuous projection of treatment light on the eye (e.g., the cornea and/or sclera) is dependent on the concentrations of the photosensitizer (both excited state and ground state) and/or the partial pressure of the oxygen in the eye (e.g., the cornea and/or sclera). In some embodiments, the filtered/unfiltered times for the discontinuous projection of treatment light on the eye (e.g., the cornea and/or sclera) is controlled manually. In another embodiment, the filtered/unfiltered times for the discontinuous projection of treatment light on the eye (e.g., the cornea and/or sclera) is automatically based on input by the physician at a control unit to determine overall treatment time and duration of filtered/unfiltered cycles. In another embodiment, the filtered/unfiltered times for the discontinuous projection of treatment light on the eye (e.g., the cornea and/or sclera) are microprocessor-controlled on the basis of the ratio of riboflavin phosphorescence at 605 nm in relation to riboflavin fluorescence at 525 nm detected from a measurement/sensor device in each treatment head. As the ratio of triplet state riboflavin phosphorescence of 605 nm/525 nm fluorescence drops, the microprocessor controls filtered/unfiltered times in accordance with the riboflavin concentration and/or oxygen partial pressure. When the light is filtered, the oxygen consumption by the riboflavin triplets stops and the cornea and/or sclera reoxygenates from the tear film or from oxygenated ophthalmic solutions applied to the eye (e.g., the cornea and/or sclera).

In some embodiments of the ophthalmic treatment systems, the light control device includes a manual or microprocessor-controlled intensity control device (e.g. a dimming mechanism or switch) so as to provide for gradual decreases and increases in the UVA light intensity. Without wishing to be bound by any particular theory, it is contemplated that the gradual intensity adjustment mitigates one or more of startling effect, fixation loss, de-centered treatment, and Bells phenomenon. In some embodiments, the dimming mechanism is configured to provide periods of decreased UVA light, such that tissue reoxygenation occurs, and periods of increased UVA light, such that cross linking occurs. In some embodiments, the dim/bright times for the adjustable projection of treatment light on the eye (e.g., the cornea and/or sclera) is dependent on the concentrations of the photosensitizer (both excited state and ground state) and/or the partial pressure of the oxygen in the eye (e.g., the cornea and/or sclera). In some embodiments, the dim/bright times for the discontinuous projection of treatment light on the eye (e.g., the cornea and/or sclera) is controlled manually. In another embodiment, the dim/bright times for the discontinuous projection of treatment light on the eye (e.g., the cornea and/or sclera) is automatically based on input by the physician at a control unit to determine overall treatment time and duration of dim/bright cycles. In another embodiment, the dim/bright times for the discontinuous projection of treatment light on the eye (e.g., the cornea and/or sclera) are microprocessor-controlled on the basis of the ratio of riboflavin phosphorescence at 605 nm in relation to riboflavin fluorescence at 525 nm detected from a measurement/sensor device in each treatment head. As the ratio of triplet state riboflavin phosphorescence of 605 nm/525 nm fluorescence drops, the microprocessor controls dim/bright times in accordance with the riboflavin concentration and/or oxygen partial pressure. When the light is filtered, the oxygen consumption by the riboflavin triplets stops and the eye (e.g., the cornea and/or sclera) reoxygenates from the tear film or from oxygenated ophthalmic solutions applied to the eye (e.g., the cornea and/or sclera).

In some embodiments of the ophthalmic treatment systems, the light control device includes a manual or microprocessor-controlled pattern control device, such as a light mask or a reticle, to provide patterned projection of the at least one treatment light onto the eye (e.g., the cornea and/or sclera). In some embodiments, the pattern control device is configured to simultaneously transmit part of the at least one treatment light such that cross linking occurs, and block the rest of the at least one treatment light such that tissue reoxygenation occurs. In some embodiments, masks or reticles of different patterns may be selectively positioned in the treatment light path to the eye and may be controlled to provide for variable durations of illumination and non-illumination, resulting in varying levels and depths of corneal and/or scleral strengthening in selected areas to impart varying levels of corneal and/or scleral refractive change. In some embodiments, the pattern control device is one or more reticles having apertures that allow a variety of different light distribution patterns and sizes to be selected by the physician. The patterns and sizes allow the physician to direct light emission to pre-selected sections or portions of the eye (e.g., the cornea and/or sclera) that benefit from corneal and/or scleral strengthening, either to strengthen weakened corneal and/or scleral tissue, or to impart selective strengthening and resulting refractive changes to improve visual acuity. In some embodiments, the patterns and durations of the patterned light projection are dependent on the concentrations of the photosensitizer (both excited state and ground state) and/or the partial pressure of the oxygen in the eye (e.g., the cornea and/or sclera).

One technical feature of the present disclosure is that the discontinuous/adjustable/patterned treatment light projection allows reoxygenation during treatment. It is found that oxygen is consumed during cross-linking and needs to be replenished, such as through the anterior corneal and/or scleral surface. When excitation energy is applied to the surface of the eye (e.g., the cornea and/or sclera), the oxygen that is reentering the eye (e.g., the cornea and/or sclera) is consumed at a rate that exceeds the reoxygenation diffusion rate and the eye (e.g., the cornea and/or sclera) remains hypoxic, particularly in the posterior portions, under continuous wave conditions. It is noted that blue light excitation gives the user an option for increased reoxygenation of the posterior stroma. Blue light is less absorbed in the anterior cornea and/or sclera and accordingly the oxygen consumption rate is lowered. This allows more of the replenishment oxygen to reach the posterior stromal region.

For example, the triplet riboflavin molecules created during photochemical therapy either form singlet oxygen created in a Type II reaction or hydrogen peroxide by a Type I reaction. In the presence of physiological amounts of oxygen of 20 mm Hg partial pressure the Type II singlet oxygen reaction predominates. Under conditions of subnormal oxygen availability (less than 5 mm Hg of O2), the Type I hydrogen peroxide reaction predominates. It is contemplated that the stromal region is hypoxic under the current protocol of continuous 3.0 mw/cm2 UVA and 0.1% riboflavin cornea. The available oxygen content of the stroma is consumed almost immediately as demonstrated by the following calculation. Given the volume occupied by a 500-micron thick cornea and the reported literature value of 35 micromolar oxygen in the stroma, the total amount of oxygen in the cornea is about 1.4×10-9 moles. The quantum yield of singlet oxygen from riboflavin irradiation is 0.52, indicating that approximately 2 photons of absorbed energy consume 1 unit of molecular oxygen. Accordingly, only 2.8×10-9 moles of photons are required to consume all of the available stromal oxygen. Using the relationship $E=h\nu$ the amount of energy to deplete all of the cornea oxygen is less than 1 mJ of UVA light. It is contemplated that oxygen is consumed rapidly (e.g. in seconds) after the treatment starts. Thus, the reoxygenation provided by the disclosed treatment system, such as through discontinuous/adjustable/patterned treatment light projection, allows improved cross-linking Photosensitizer/Oxygen Monitor In some embodiments, the ophthalmic treatment systems includes a device for monitoring the concentration of the photosensitizer (e.g. riboflavin, rose Bengal, other photosensitizers, or derivatives thereof) in the eye (e.g., the cornea and/or sclera) so the physician may discontinue, adjust, or selectively apply the at least one treatment light to achieve the optimal depth of penetration while still reducing the risk of damage to the endothelial cells. In addition, the photosensitizer monitor also allows the physician to determine when sufficient riboflavin is present in the eye (e.g., the cornea and/or sclera) during light treatment. In some embodiments, an optical collection device is mounted adjacent to the optical head and is configured to collect photoluminescent emissions from the eye (e.g., the cornea and/or sclera) during treatment. The output of the optical collection device is connected to a photoluminescence monitoring unit.

Without wishing to be bound by any particular theory, it is contemplated that knowledge of the amount of photoluminescence allows the physician to adjust the treatment to reduce the potential loss of endothelial cells by excess UV radiation, which is attributable to low concentration of the riboflavin, excessive treatment light intensity, toxic peroxides or reactive oxygen species (ROS) generated under hypoxic conditions, or combinations thereof. In addition, without wishing to be bound by any particular theory, it is contemplated that excessive riboflavin in the eye (e.g., the cornea and/or sclera) not only prevents significant amounts of UV from reaching the endothelial cells in a sunscreen-like effect, but also limits the cross-linking depth to the anterior portion of the stroma. Measurement of riboflavin concentration allows the physician to monitor for excessive riboflavin during the procedure and to take appropriate steps to mitigate such conditions.

In some embodiments, the photosensitizer monitor is based upon the detection of the photoluminescence of the photosensitizer as it interacts with the excitation light. As used in the present disclosure, "photoluminescence" is defined as the combined radiation given off by the fluorescence of photosensitizer and the radiation given off as phosphorescence from the excited state of the photosensitizer (e.g. triplet state of riboflavin). The emission intensity of the photoluminescent radiation is a function of the light wavelength, the light intensity and the concentration of the riboflavin. Since the wavelength and intensity of the applied light is known, the emission intensity of photoluminescent radiation from the patient's eye (as determined by the photoluminescence monitoring unit and a suitable microprocessor receiving the output of the monitoring unit) is used to measure the riboflavin concentration. In some embodiments, the photosensitizer monitor uses colorimetry (e.g. color comparison charts) to determine the concentration of the photosensitizer.

In some embodiments, the photosensitizer concentrations measured are provided to the physician on a display unit associated with the system to allow the physician to adjust the treatment light intensity or wavelength, switch to discontinuous light projection, or take other steps in response to detected reduction or increase in concentration of riboflavin.

In some embodiments, the ophthalmic treatment systems further comprises a device for monitoring molecular oxygen or oxygen partial pressure in the eye (e.g., the cornea and/or sclera). In some embodiments, the oxygen monitor is based on the triplet state riboflavin phosphorescence at 605 nm in relation to riboflavin fluorescence at 525 nm. As the ratio of triplet state of riboflavin phosphorescence of 605 nm/525 nm fluorescence decreases, the quantum yield of the triplet state molecules decreases, thereby indicating a decrease in the partial pressure of oxygen in the eye (e.g., the cornea and/or sclera).

Without wishing to be bound by any particular theory, it is contemplated that, during the course of the irradiation, the riboflavin photo-oxidizes and degrades to a form that does not fluoresce or create triplet molecules. Under ideal conditions, the phosphorescence would degrade at the same rate. However, the presence of oxygen is required for phosphorescence of riboflavin to occur in solutions, and oxygen also quenches the phosphorescence of the riboflavin. The quenching of the phosphorescence by oxygen corresponds to the reduction in the phosphorescence signal. Since some degradation in the triplet phosphorescence signal is expected as a result of riboflavin degradation, the optimal index for monitoring the oxygen quenching of triplet riboflavin is the ratio of the phosphorescence to the fluorescence. The phosphorescence signal is compared to the fluorescence signal during calibration and expressed as a ratio (e.g. 30:100). As the reaction proceeds over time, the ratio decreases as the phosphorescence signal decreases, indicating quenching of triplet riboflavin by molecular oxygen. In some embodiments, the decrease in the ratio is used as a proxy measure of the singlet oxygen production. As the ratio of the phosphorescent/fluorescent signal decreases, the efficiency of singlet oxygen production decreases, allowing the ratio to level off at some point, which signals to the operator the need to reoxygenate the eye (e.g., the cornea and/or sclera) by discontinuous/adjustable/patterned light projection.

Projection Distance

In some embodiments, the projection optics are configured to provide a distance of the patient's eye from the optical head of approximately two inches or greater. Other working distances, such as about three inches or from about three inches to about six inches, are provided in alternative embodiments. The increased working distance between the optical head and patient's eye provides improved physician visualization and better access to the eye during treatment, for example to add more photosensitizer drops or other ophthalmic solutions, or for other treatment aids.

Fixation Light

In some embodiments, the ophthalmic treatment systems further comprises a fixation light either attached to or separated from the treatment device. During periods of continuous or discontinuous/adjustable/patterned light projection, the patient's eyes naturally deviate from the desired position. Fixing the patient's line of sight, such as on a fixation light, allows the patient's eyes to remain correctly aligned and/or focused. In some embodiments, the fixation light is independently movable in relation to the optical treatment head(s) to fix the patient's eyes at certain directions and/or angles, thereby allowing the physician to deliver light in a beam path/direction that is independent of the patient's visual axis. In some embodiments, the fixation light is positioned within the line of sight of both eyes of the patient, at a distance from each eye that is sufficient to prevent double vision of the fixation light. In some embodiments, the fixation light emits red light, or other light within the visible spectrum such as green light, which is easily viewable by a patient during treatment. In another embodiment the fixation light periodically blinks or emits an audio cue to reacquire and/or maintain the patient's attention.

Auxiliary Light Source

In some embodiments, the ophthalmic treatment systems comprises another light source in addition to the UVA/blue treatment light which is turned on/off coincident with the at least one treatment light entering a period of discontinued/filtered/dimmed or entering a period of continued/unfiltered/non-dimmed light. In some embodiments, the additional light emission is integral to the UVA/blue treatment light path and at least partially compensates for the changes in color and light intensity seen by patients during periods of varying UVA/blue illumination, reducing the startle effect when the UVA or blue treatment bean is turned on and off. In some embodiments, the separate light source has a wavelength in the visible light spectrum that is not highly absorbed by riboflavin and therefore does not result in oxygen consumption from riboflavin triplet formation, yet appears to the patient to be of the same or similar color as that of excited riboflavin. In some embodiments, the auxiliary or anti-startle light source may be a green light LED. Without wishing to be bound by any particular theory, it is contemplated that the gradual intensity adjustment mitigates one or more of startling effect, fixation loss, de-centered treatment, and Bells phenomenon.

Light Source

In some embodiments, the treatment device comprises a multi-wavelength light source. In some embodiments, the multi-wavelength light source is a full-spectrum light source that is filtered to give a narrow band of excitation energy within the UVA/blue light spectrum, and is controllable to provide output light in at least two different wavelengths. In some embodiments, the light source is a short-arc lamp such as a mercury or mercury halide lamp or a short-arc xenon lamp, which emits UVA light as well as light in other wavelengths. In some embodiments, the light source unit further comprises an optical system which isolates light to a light beam in the wavelength required for treating the patient and provides the isolated light beam to the light guide for transmission to the optical treatment head. In some embodiments, the optical system comprises a focusing device for focusing radiation from the lamp along an optical path and a beam isolating assembly in the optical path which is configured to direct light in a selected wavelength range into the first end of the light guide. In some embodiments, the beam isolating assembly comprises a reflective dichroic mirror which reflects light in the UVA/blue range of around 340 nm to 470 nm and passes other radiation emitted by the lamp, and a filter in the path of reflected light from the mirror which directs light of a predetermined wavelength or wavelength band to the wavelength control device.

In some embodiments, the light source is one single or limited wavelength light source or multiple single wavelength light source, and may be one or more light emitting diodes (LED) or laser diodes and provides isolated light beams at selected wavelengths or limited wavelength ranges.

Wavelength Control Device

In some embodiments, a wavelength control device selectively provides light at one or multiple wavelength bands for treatment purposes (e.g. light in a UVA band and/or light in a blue or blue-violet band). In some embodiments, two different filters are provided which are selectively positioned in the light path, allowing selection of excitation energy in the UVA band at 365 nm, or a narrow band of blue-violet radiation at 405 nm. The option of UVA or blue radiation allows the surgeon flexibility in achieving different depths of penetration into the cornea and/or sclera for the excitation light. For example, the molar extinction coefficient of riboflavin at 365 nm is about 10,000 and at 405 nm, the extinction coefficient is about 8000. If the riboflavin in the cornea and/or sclera is 0.003 molar, the 365 nm radiation deposits about 75% of its energy to the riboflavin in the first 200 microns of the tissue, whereas with the 405 radiation only about 68% of the beam is absorbed in the first 200 microns. The blue light delivers more energy in the deeper tissue for deeper cross-linking. For patients with thin corneas and/or sclera, the UVA is used in some embodiments since the energy is absorbed more quickly and less energy reaches the endothelium. For patients with thicker corneas and/or scleras, blue light is used in some embodiments to penetrate deeper into the cornea and/or sclera. In a conventional procedure that uses 365 nm radiation, deepithelialization and 0.1% riboflavin soaking, cross-linking occurs to a depth of about 200 microns, while damage (apoptosis) occurs deeper, at about 300 microns. The multi-wavelength excitation option of the disclosed system allows for deeper cross-linking (e.g. by blue light) if the surgeon determines deeper cross-linking is beneficial or necessary. This technical feature is heretofore unknown as currently marketed systems use monochromatic LEDs and do not allow for selectable excitation wavelengths.

One technical feature of the present disclosure heretofore unknown is the option to select one of multiple wavelengths of the excitation light. Without wishing to be bound by any particular theory, it is contemplated that the wavelength determines the depth of penetration of the light into the riboflavin soaked cornea and/or sclera, which in turn affects how much cross-linking is done at different depths of the corneal stroma or sclera. The molar extinction coefficient of riboflavin is 10,066 cm-1/M at 365 nm but the molar extinction coefficient of riboflavin is only 7884 cm-1/M at 405 nm. Under the Beer Lambert law, for a given wavelength and excitation energy, the fluorescent intensity of the photosensitizer (e.g. riboflavin) is linearly proportional to the concentration of the fluorophore. Calculation of the light absorption by riboflavin at various depths of the cornea and/or sclera of the two wavelengths is possible using the Beer Lambert equation. In this equation $A=2-\log 10\% \ T$, where A is the absorbance of energy by a chemical fluorophore and T is the transmission. The Beer Lambert law states that $A=Ebc$ where E is the molar extinction coefficient for a particular chemical and b is the path length of the measurement and c is the concentration of the chemical. For a 0.1% solution of riboflavin at a depth of 500 microns the absorption value at 365 nm is calculated as $A=1.10$. The value of A for the same solution and path length for 405 nm radiation is calculated as $A=0.86$. From the formula $A=2-\log 10\% \ T$ it is shown that 64% of the incident energy of 365 nm radiation is absorbed by riboflavin in the first 200 microns of the cornea and/or sclera. The same calculations at 405 nm indicate only 55% of the radiation is absorbed by the riboflavin in the first 200 microns of the stroma or sclera. If the user determines that it is desirable to cross link deeper into a cornea and/or sclera, the user has the option to select a more penetrating radiation like 405 nm. If shallow cross-linking is more desirable, the user has the option to select a less penetrating wavelength, such as 365 nm.

An additional feature of the 405 nm wavelength is the option to use less intense light to accomplish the same amount of cross-linking. The production of singlet oxygen by excited riboflavin triplet molecules is related to the number of incident photons, not the energy of the photons. Riboflavin is excited at both 365 nm and 405 nm to its higher energy states. By the formulation $E=h\nu$ it is determined that a 405 nm photon is 10% less energetic than a 365 nm photon, and that to have equivalent stoichiometric reactions at 405 nm and 365 nm the incident UVA light fluence is reduced to 90% of the blue light fluence.

Another additional feature of the blue light option for excitation energy is that the lower absorption of blue light by riboflavin in the anterior cornea and/or sclera translates into less oxygen consumption in the anterior stroma or sclera, and thereby allowing better reoxygenation of the posterior stroma or sclera, as discussed in more detail below.

Optical Coupling

In some embodiments, two components in the ophthalmic treatment systems are optically coupled together through transmission of light from one to another. In some embodiments, at least some of the components in the ophthalmic treatment systems are optically coupled together through at least one UV transmissive liquid light guide to produce homogeneous light distribution. In some embodiments, the light source is coupled to the wavelength control device through the liquid light guide. In some embodiments, the wavelength control device is coupled to the optical treatment head(s) through the liquid light guide. In some embodiments, multiple liquid light guides or a bifurcated light guide are used in bilateral systems. Liquid light guides are also more efficient in transmitting light and provide cold light, avoiding the potential problem of hot spots. The flexible light guides also provide for variation in optical head spacing in a bilateral system, and allow for 3D movement of the optical head or heads if desired.

In some embodiments, other optical coupling apparatus is used for optical coupling of components in the ophthalmic treatment systems as alternative to or in combination with the liquid light guide. Those optical coupling apparatus include, but are not limited to mirrors, reflective prisms, refractive prisms, optical gratings, convex lenses, concave lenses, etc. In some embodiments, the treatment light sources are provided in one or more treatment heads and treatment light is projected directly from the light source or sources along an optical path to a treatment light output port of the treatment head.

Bilateral Treatment

In some embodiments, the ophthalmic treatment systems is monocular, with a single optical treatment unit including the optical treatment head. In other embodiments, the ophthalmic treatment systems is bilateral, with two optical treatment units adjustably mounted on a support stand for treatment of both eyes simultaneously. In some embodiments, the optical treatment head(s) is configured to focus a UVA or blue light beam on a patient's eye. In other embodiments, the optical treatment head(s) incorporates additional treatment or monitoring devices. In some embodiments, the optical treatment heads are identical but are separately mounted to allow for adjusting the distance between the treatment heads. In another embodiment, more than two treatment heads are used in the ophthalmic treatment systems. In some embodiments, the optical treatment heads allow for independent angular adjustment, adjustment of the distance separating the optical treatment heads, and/or adjustment of the distance between the treatment heads and the eyes. In some embodiments, the optical treatment heads are configured to allow for angular variations as well as distance variations of the at least one treatment lights. Without wishing to be bound by any particular theory, it is contemplated that the independent angle and distance adjustment allows treatment of strabismus (crossed eyes) and/or allows selective treatment (e.g. crosslinking) of specific areas of the cornea and/or sclera based on pathology of the condition to be treatment or location of the refractive correction desired.

In some embodiments, the light guide from the light source unit or the wavelength control device is bifurcated to provide two separate light guide portions which direct UVA or blue treatment light beams from the respective optical treatment heads. Treatment light is projected onto the cornea and does not require collimation.

The foregoing systems and methods allow the physician to better monitor the patient's eye during treatment. Some embodiments allow monitoring of critical variables during treatment as well as variation of the treatment criteria, for example switching between UVA and blue or blue-violet light, varying the light intensity, providing a fixation light to prevent eyes from wandering, utilizing an additional light source to prevent the startling effect, varying the beam shape and size, and using a discontinuous/adjustable light projection to allow for tissue reoxygenation. Another technical feature of the system is that distance of the optical head from the eye is accurately controlled. The system is easy to set up and use, and allows a high degree of control and customization of treatment to a specific patient condition.

Non-Limiting Examples

Certain embodiments as disclosed herein provide for an ophthalmic treatment system and method.

After reading this description it will become apparent to one skilled in the art how to implement the present disclosure in various alternative embodiments and alternative applications. However, although various embodiments of the present disclosure will be described herein, it is understood that these embodiments are presented by way of example only, and not limitation.

Figure 2:
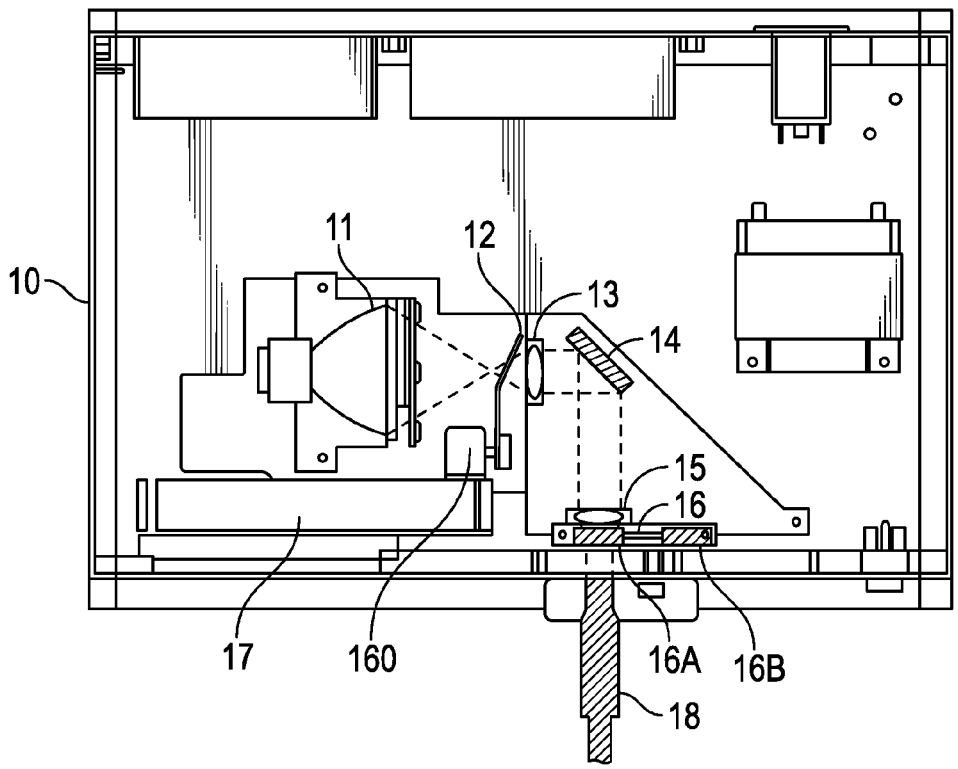
FIG. 2 is a block diagram illustrating the optical source unit of FIG. 1.

FIGS. 1 to 12 illustrate one embodiment of a bilateral system for photochemical ocular treatment such as corneal and/or scleral collagen cross-linking using riboflavin as a photosensitizer. In this embodiment, UVA/blue light is used for the excitation energy. Referring to FIGS. 1 and 2, an illumination source unit 10 contains a multi-spectral light source 11 that delivers a user-selected excitation wavelength to bifurcated, UV transmissive liquid light guide 18. The light guide splits into separate light guide outputs 21 and 22 that are connected to illumination intensity adjustment module 30 mounted on a mobile pole stand comprised of pole 25 mounted on a base 23 with casters. Other support stands of different configuration are used in place of pole 25 with base 23 in alternative embodiments. Outputs of module 30 are connected by light guides 50, 51 to respective left and right optical treatment devices or units 150, 151. The right treatment device 151 is described in more detail below in connection with FIGS. 9 and 10. The left treatment device 150 is identical to the right treatment device 151.

The pole allows attachment and vertical positioning of an adjustable mounting mechanism including articulating arm 24 on which the treatment devices 150, 151 are mounted, and provides mounting points for illumination intensity adjustment module 30 and an optical monitoring module 40. Modules 10, 30 and 40 are combined in a single unit in other embodiments. The illumination source unit 10 is shown as separate from the mobile stand but is affixed to the stand in another embodiment. The end of articulating arm 24 connects to rotating arm 27 which further connects to rotating arm 28. The distal end of rotating arm 28 carries the two optical treatment devices or units 150, 151 encased in housing units 260, 261 on adjustable arms 29A, 29B. Each housing unit includes an externally mounted sensor 158, 159. Each housing unit holds in place an optical treatment device 150, 151. Each optical treatment device includes an optical treatment head 81 which directs light onto the patient's eye, in addition to other components described in more detail below in connection with FIGS. 9 and 10. In some embodiments, light guides 18, 21, 22, 50 and 51 which conduct the excitation energy to each optical treatment head are liquid light guides, because the water-based liquid in the light guide absorbs infrared radiation from the lamp source that could adversely affect tissues. Liquid light guides generally have greater transmission efficiency for UV and visible light than fiber bundles while providing greater flexibility to allow for adjustment of the position of each treatment unit. An additional benefit of using liquid light guides is that they are effective in homogenizing light beams collected from non-homogeneous light sources or reflectors. In alternative embodiments, the light sources and other system components may be mounted in the respective treatment heads.

FIG. 2 illustrates the layout of the illumination source assembly with an ellipsoidal reflector short-arc lamp 11 as the light source, as in the first embodiment. In some embodiments this lamp is a 100 watt short-arc mercury or mercury halide lamp. In a different embodiment, this lamp is a 100 watt short-arc xenon lamp that is characterized by a lower UVA output and a greater continuum of high intensity blue wavelength light. Microprocessor 17 controls the opening and closing of light modulating device (for example, a shutter and/or filter) 12 that either blocks or allows passage of radiation emitted from the lamp. Light modulating device (for example, a shutter and/or filter) 12 is a mirrored aluminum material to reflect radiation away from the optical path. The reflective quality of the material prevents a heat buildup on the shutter and potential transfer of heat to the connecting solenoid assembly. The light modulating device (for example, a shutter and/or filter) 12 is affixed to a rotary solenoid 160 to affect the opening and closing operation. Rotary solenoids are high reliability components with normal lifetimes exceeding 1 million cycles. When light modulating device (for example, a shutter and/or filter) 12 is opened, the light from the lamp reflector is collected by collimating lens 13 and directed to dichroic 45 degree turning mirror 14 that reflects UVA and blue light in a wavelength range of around 340 nm to 470 nm, while passing infrared radiation. The reflected light from the mirror is collected by focusing lens 15 and directed through one of the filters on filter assembly 16 into the input of bifurcated light guide 18. Filter assembly 16 is on a slide mechanism connected to an actuating switch on the front panel. Two narrowband band pass filters 16A, 16B are mounted on the optics filter assembly 16 and an actuating switch position determines which band pass filter is placed in front of the light guide. In some embodiments, filter 16A is a UVA filter that has a 10 nm bandwidth (FWHM) at 365 nm and filter 16B has a 10 nm bandwidth (FWHM) at 405 nm. Such filters are commercially available from various optical suppliers.

Various adjustable features of the system described below involve manual input by an operator at the various units in order to vary operating conditions, such as intensity adjustment via module 30, selection between the UVA and blue light filters 16A and 16B, and positioning of the optical treatment heads. In an alternative embodiment, these features are adjusted by an operator by input at remote input device or keyboard, and the controller in this alternative has control outputs to the selectable filter assembly 16A, 16B, and intensity adjustment module 30. An automatic emergency shut off feature is provided in some embodiments.

Figure 3:
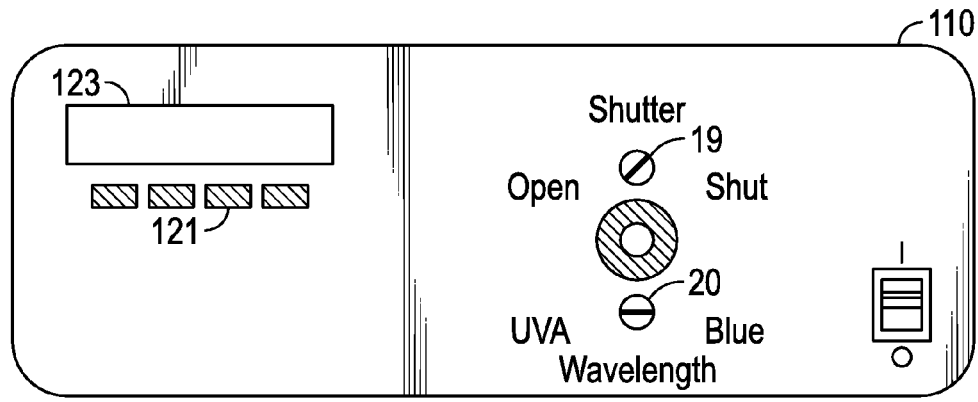
FIG. 3 is a view of an embodiment of the front control panel of the illumination source unit of FIG. 2.

FIG. 3 illustrates one embodiment of a control panel 110 provided on the front of illumination source unit 10 including user input devices and display unit 123. In other embodiments, the controller is a standalone desktop or laptop computer, or a personal digital assistant or the like, with a standard display unit and a keyboard input device for user input control selections for the various selectable control parameters of the system, which is transmitted by wired or wireless communication signals to control various system components. Panel 110 has a manual wavelength selection control switch 20 to allow an operator to switch between UVA and blue light, and a manual light modulating device (for example, a shutter and/or filter) control switch 19 to switch between continuous and discontinuous illumination. Soft key inputs 121 below display 123 on the panel are used by an operator to control the light modulating device (for example, a shutter and/or filter) cycle. The soft keys are switches that change function as the display changes.

Figure 4:
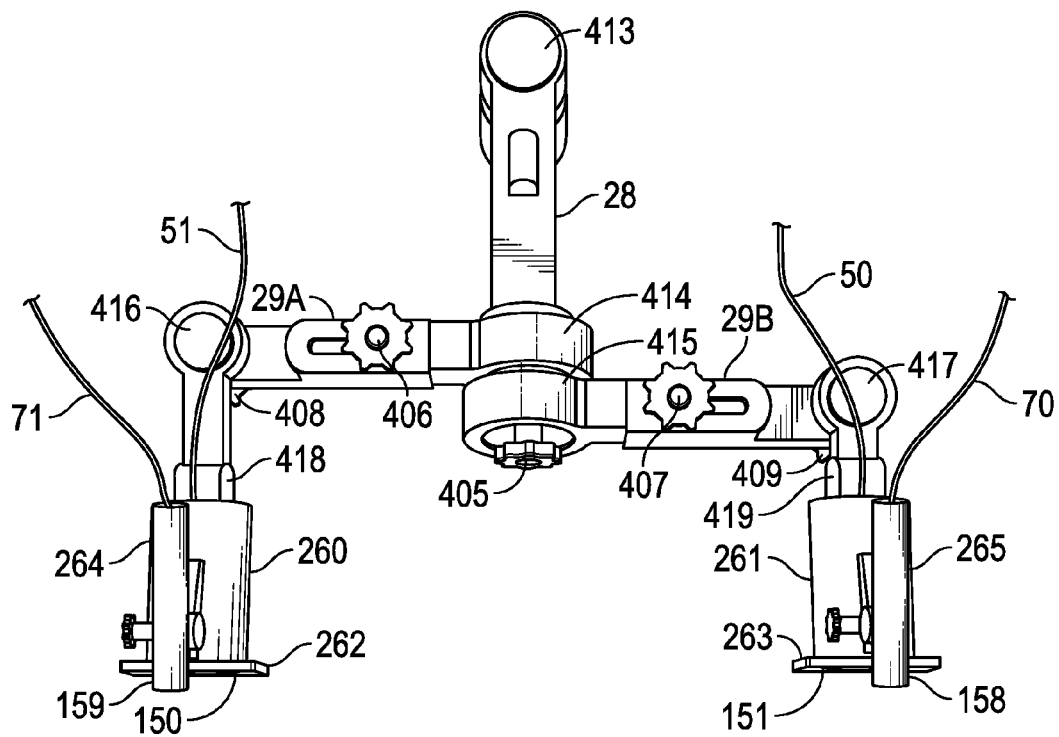
FIG. 4 is a top perspective view of the bilateral optical head of FIG. 1.

Referring to FIGS. 1 and 4, the mobile pole stand with the mounted articulating arm and height adjustment wheel, provides for easy positioning of the optical treatment heads over the patient's eyes.

FIG. 4 is an enlarged top plan view of the articulated arm assembly and treatment devices 150, 151 of FIG. 1. The height adjustment wheel 26 shown in FIG. 1 provides for vertical adjustment of the arm. Lateral adjustment of the optical heads to accommodate different interpupillary distance is provided by the pivot arms 29A, and 29B on the distal end of the articulating arm, as illustrated in FIG. 4. When knob 405 is loosened, both arms 29A and 29B are free to pivot around the center of arm 28 and knobs 406, 407 are loosened to telescope arms 29A, 29B to adjust the interpupillary distance and to align each optical head with the respective eyes of a patient. When optical heads on arm 29A, 29B are positioned over the eyes of the patient, knobs 405-407 are tightened to fix the position. Heads 260 and 261 are still movable at this point and a combined movement of the heads allows for XY axis adjustment of the optical heads over the patient's eyes for bilateral operation. Knobs 408 and 409 are tightened to secure the position of the optical heads over the patient's eyes. In alternative embodiments, the manual positioning knobs are eliminated and another system is provided for vertical and horizontal positioning of the treatment heads.

In alternative embodiments, the manual positioning knobs are eliminated and a remotely controlled drive system is provided for vertical, horizontal, and angular positioning of the treatment heads. X, Y and Z direction positioning are then controlled remotely by the operator via a computer input device, touch screen or the like, or are carried out automatically on entry of patient eye parameters by the physician, for example as described below in connection with the embodiment of FIGS. 23 to 29.

In the ophthalmic treatment system of FIGS. 1 to 11, the at least one treatment light beam of each optical head is directed concentric to the optical axis passing through the center of the cornea to the center of the lens in some embodiments. It is desirable in some circumstances to position the light beam on an optical axis different than the corneal-lens optical axis. For example, if the apical distortion from keratoconus is in the inferior portion of the cornea, it is desirable to place the optical axis of the illumination beam concentric with the central axis of the apical distortion in some embodiments to maximize the radiation concentrically around the apical distortion. FIGS. 8A and 8B illustrate one example of the apical distortion of keratoconus compared to a normal cornea. FIG. 8A illustrates an eye 500 with a normal cornea 502, with the dotted line 504 representing the optical axis passing through the center of the cornea. FIG. 8B illustrates eye 500 with keratoconus causing an off-axis conical distortion and resultant thinning of the cornea at 506. This requires an XYZ positioning flexibility for the optical head, and this is achieved in one embodiment by the mechanical arrangement shown in FIG. 4 as described above.

The output light intensity adjustment for each eye in the system of FIGS. 1 to 17 is accomplished using the intensity adjustment module 30 illustrated in layout view in FIG. 7. Mechanical brackets are affixed to the output light guides and these brackets are connected to commercial screw-driven linear slides 31 and 32. The bifurcated input light guide ends 21 and 22 are fixed at the bottom of the module. Turning the externally accessible knobs on slides 31 and 32 clockwise advances the delivery light guides 50 and 51 toward the input light guides and increases the intensity of the output. Likewise, turning the knobs in a counterclockwise direction reduces the intensity. The output is measured by using an external hand held radiometer under the output optics. Appropriate radiometers for UVA or blue light are commercially available from a variety of sources. Adjustment of the output of each optical head within 0.01 mw/cm2 is obtained in this embodiment. In another embodiment, adjustable neutral density filters are placed between the input and output light guides but these filters are often subject to long term UVA deterioration. FIG. 7 illustrates the maximum intensity adjustment for excitation light guide 51 and the minimum intensity adjustment for excitation light guide 50.

In the illustrated embodiment, a manually operable switch 55 allows a user to convert from bilateral to monocular operation. Switch 55 is connected to light modulating device (for example, a shutter and/or filter) 56. In the position of light modulating device (for example, a shutter and/or filter) 56 as shown in FIG. 7 the light entering from light guide 21 is blocked from entering the delivery light guide 51 and the instrument is set for monocular operation. When the switch is rotated from this position, the light modulating device (for example, a shutter and/or filter) rotates out of the light path and closes a microswitch. Light now travels to both output heads and the closed microswitch completes a circuit to light an LED on top of the module alerting the user that the instrument is in bilateral mode. In alternative embodiments, the manual switch is replaced by a remote control device such as a computer module with a user control input or touch screen for switching between bilateral or monocular operation. The same control input is used in some embodiments to enter commands to vary other adjustable features of the system, such as the excitation energy frequency, intensity, continuous or discontinuous illumination, treatment period, treatment head height, separation, and angle, and the like.

Figure 5:
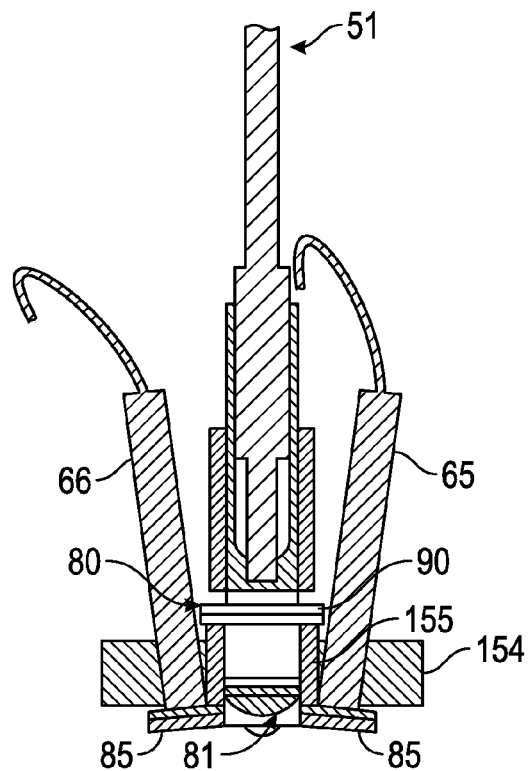
FIG. 5 is a cross-sectional view of an embodiment of an optical treatment head.
Figure 9:
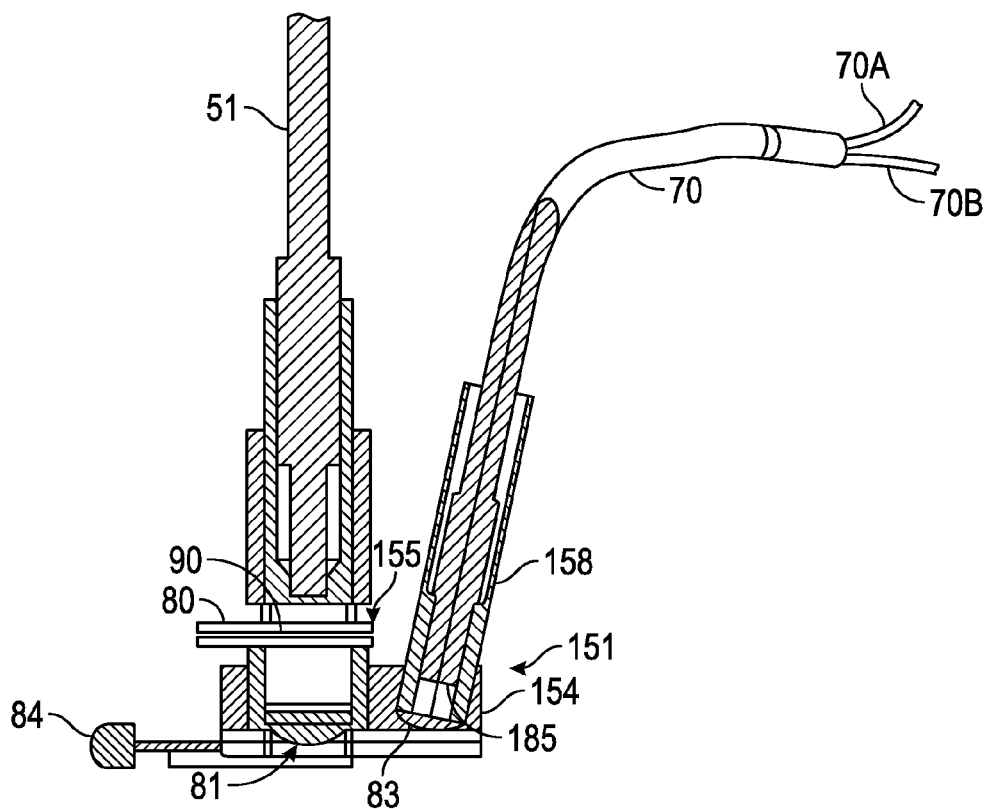
FIG. 9 is a side cross sectional view of the left hand optical delivery and sensor head of FIG. 4.
Figure 10:
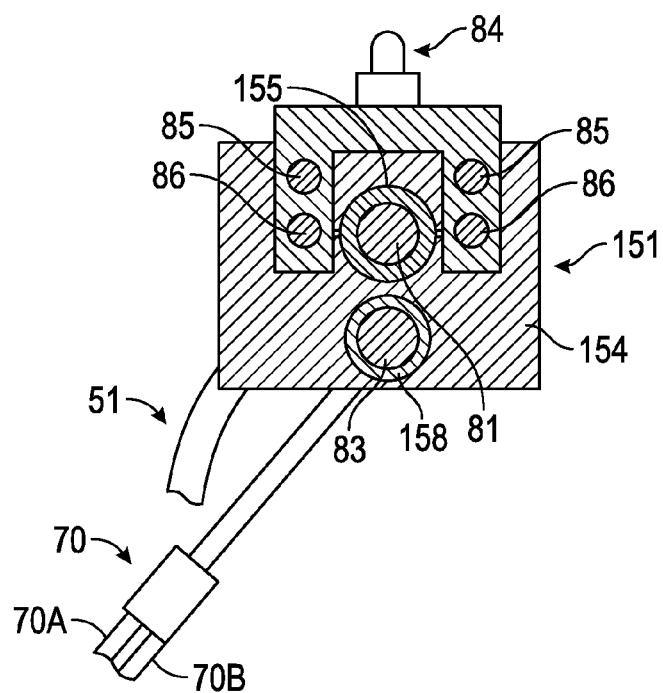
FIG. 10 is a bottom view the left hand optical delivery and monitoring head of FIG. 4.

One of the optical treatment devices 151 is illustrated in more detail in FIGS. 5, 9 and 10. As illustrated, each optical treatment device comprises optical treatment head 155 vertically mounted on support 154 at the end of the respective arm 29A or 29B, and optical collection device 158 also mounted on support 154 adjacent the optical treatment head 155, as illustrated in FIG. 9. Treatment head 155 incorporates an optical mask or reticle holder 80 in which a selected reticle or mask 90 may be positioned for controlling shape and/or size of the output treatment beam projected from treatment head 155 via projection optic or lens 81 located at the output port of the treatment head. Aiming or positioning apparatus 65, 66 mounted in each optical treatment unit 150 and 151 assists an operator in positioning the projection optic or lens 81 at a desired working distance from the cornea. In the embodiment of FIGS. 5, 9 and 10, the aiming devices 65, 66 are laser diodes. The distance of optic 81 from the cornea is determined to be equal to the desired working distance when the two aiming beams from laser diodes 65 and 66 coincide with each other as a single spot on the patient's eye. If the aiming beams do not cross at the eye, the height adjustment knob 26 on the articulating arm can move the optical heads up or down until the beams coincide at the correct position. This provides a more accurate method for positioning the optical heads at a predetermined distance relative to the patient's eyes.

In one embodiment, filters 85 or 86 may be selectively positioned in the path of the aiming beams emitted from aiming devices 65, 66 via mechanical slide 84 (see FIG. 10). This may provide a secondary use to the aiming beams for providing red light phototherapy to ameliorate oxidative damage to the cells. In another embodiment, the aiming devices 65, 66 may be red or green light laser diodes with no filters in the output path.

Figure 11:
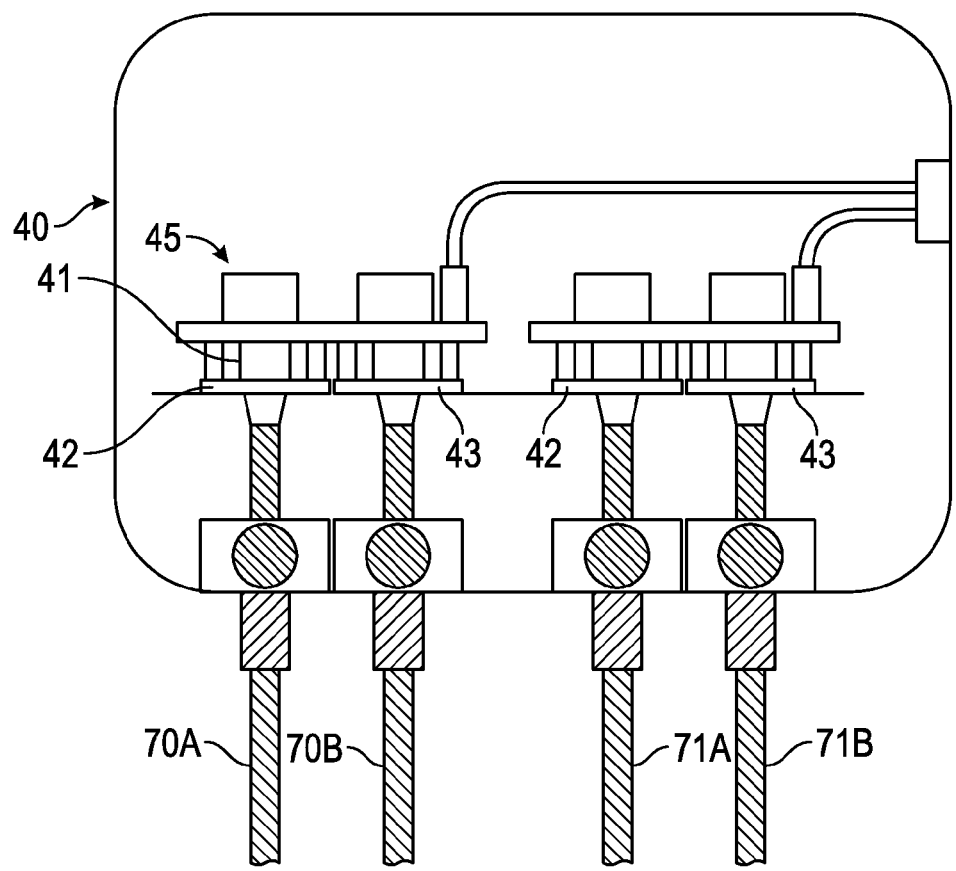
FIG. 11 is a component layout view of one embodiment of a photo luminescent measuring module in the system of FIGS. 1 to 10 and 15, with the inputs from the bifurcated light guides from each optical head and the photodiodes and amplifiers for monitoring the fluorescence and phosphorescence from each eye.

In some embodiments, the ophthalmic treatment system also includes monitoring system 40 for the photoluminescence emitted from the riboflavin interaction with UVA/blue light, using optical collection device 158 as illustrated in FIG. 9. This photoluminescence consists of fluorescence from the riboflavin photonic emission from the S1 to S0 state and phosphorescence emitted from the triplet riboflavin state. These photoluminescent emissions allow measuring of riboflavin concentration in the eye (e.g., the cornea or sclera), a relative measure of the depth of penetration of the riboflavin into the stroma, a relative measure of the lateral homogeneity of the riboflavin and a relative measure of the oxygen utilization and triplet state formation. The reaction of riboflavin and UVA/blue radiation involves two electronically excited states of riboflavin. When ground state S0 (unexcited riboflavin) absorbs UVA/blue light it transitions into an excited state called the S1 state. From the excited S1 state, the molecule loses its energy by two mechanisms. The first mechanism is the relaxation back to the ground state by emitting a photon of light in a process called fluorescence. The peak fluorescence of riboflavin is about 525 nm. The average quantum yield for riboflavin in aqueous solutions is about 0.3, meaning that the ratio of photons emitted/photons absorbed is about 0.3. The second mechanism for relaxation from the S1 state is called the formation of triplet riboflavin and this is accomplished by a mechanism called intersystem crossing. The triplet state of riboflavin imparts energy to molecular oxygen and creates singlet oxygen for crosslinking. From this triplet state the riboflavin molecule can react and give up the excess energy to oxygen or water, or it can phosphoresce to the ground state. The phosphorescence of triplet riboflavin occurs at around 605 nm. Since phosphorescence is a direct measure of the active species that creates singlet oxygen, optical collection device 158 and optical monitoring device 40 of FIG. 11 are configured to monitor both the fluorescent and phosphorescent signals.

Optical collection device 158 of FIG. 9 comprises light collection lens 83 and bifurcated light guide 70 which receives the light collected by lens 83. This bifurcated light guide has one single end that splits into two output ends 70A, 70B. The lens 83 is directed to the center of the eye (e.g., the cornea or sclera) treatment zone and receives the photoluminescent emissions from the eye (e.g., the cornea and/or sclera) and focuses these emissions to the proximal or receiving end 185 of the single-ended portion 70 of the bifurcated light guide. The light guide in some embodiments provides 50% of the proximal input light into each of the two distal light guide portions 70A, 70B. The distal portions of the light guides are routed to the optical monitoring module 40 shown in layout view on FIG. 11. The optical heads or ends 185 on each of the light guides 70, 71 of the treatment devices 150 and 151 receive the photoluminescent emissions from the irradiated corneas and/or scleras of the patient's left and right eyes, and the emission light is transmitted by light guides 71 and 70, respectively, into left eye guide portions 71A, 71B and right eye guide portions 70A, 70B. The photoluminescent emission from each eye includes both fluorescence and phosphorescence due to different types of riboflavin interactions, as discussed in detail below. The emission light is directed onto filters 42 and 43 for separating fluorescence emission from phosphorescence emissions for each eye, as illustrated in FIG. 11. Filter 42 is a narrowband band pass filter with a center wavelength of 525 nm-535 nm to capture the peak of the fluorescence emission from the riboflavin. Filter 43 is a narrowband band pass filter centered at 600 nm-605 nm to capture the peak of the phosphorescence of the triplet riboflavin. By splitting the emissions collected from each eye being treated, both the phosphorescence and fluorescence for each eye are monitored in some embodiments. The filtered emission light from each light guide is directed onto a respective sensor 41, which comprises a PIN silicon photodiode 41 that incorporates an integral preamplifier or thermoelectric cooling, and the output voltage of the photodiode is transmitted to high impedance amplifier 45 for conversion of the photonic energy into voltage. Alternatively, items 41 and 45 are purchased as an integral unit from commercial sources such as Thorlabs and are capable of detection of signals as small as a few femtowatts ($10^{-15}$ watts).

Figure 12:
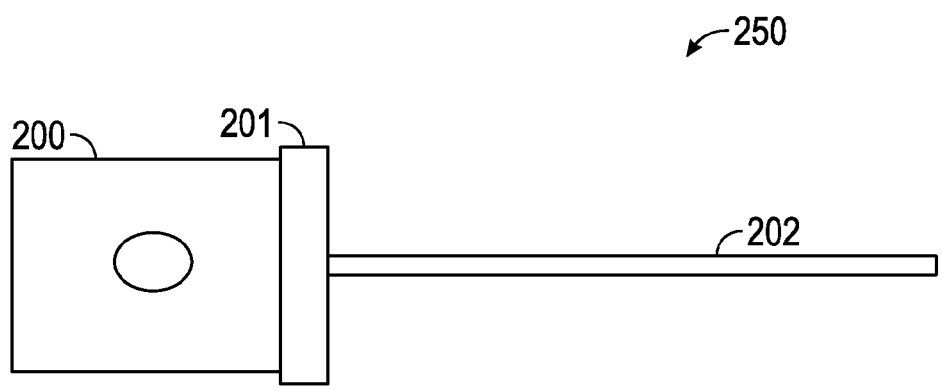
FIG. 12 shows a top view of one embodiment of a dodging tool for use in evaluating lateral riboflavin dispersion in conjunction with fluorescent intensity monitoring.

FIG. 12 illustrates one embodiment of a hand held dodging fixture or tool 250 that may be used to provide a relative measure of the lateral dispersion of riboflavin in the eye. Tool 250 has a handle 202 with a plastic holder 201 at one end which holds a UV transparent/visible blocking glass with a 3 mm hole drilled at its center. Commercial glasses such as Schott UG 11 and Schott BG 4, respectively, are suitable for use with UVA and blue treatment light, respectively. The only emitted light to reach the collection device 158 is via the hole in the center of glass 200. The dodging fixture may be held over the central cornea and the resultant fluorescence reading from the optical monitoring module 40 then reflects emissions from only a limited area of the cornea. The fixture can be moved over different areas of the cornea to obtain readings relative to the central area and other areas. This tool can therefore provide a relative quantitative measure of lateral dispersion of riboflavin in the eye. If readings show that more riboflavin than the peripheral areas, the physician may choose to wait for a longer period for the riboflavin to disperse, or may take other action to promote dispersion, e.g. placing a warm cloth over the closed eye for a few minutes.

In some embodiments, the phosphorescence of the riboflavin triplet state is used to monitor the efficiency of the reaction particularly with relation to singlet oxygen formation. Each eye is monitored for both fluorescence and phosphorescence using optical collection devices 158 and photoluminescence monitoring unit 40, as described above. The light modulating device (for example, a shutter and/or filter) 305, 315 in FIGS. 13 and 14 provides discontinuous light projection and the operation of the light modulating device (for example, a shutter and/or filter) cycle in one embodiment is directed by the operator by the soft key inputs on the control panel shown in FIG. 3.

Figure 6:
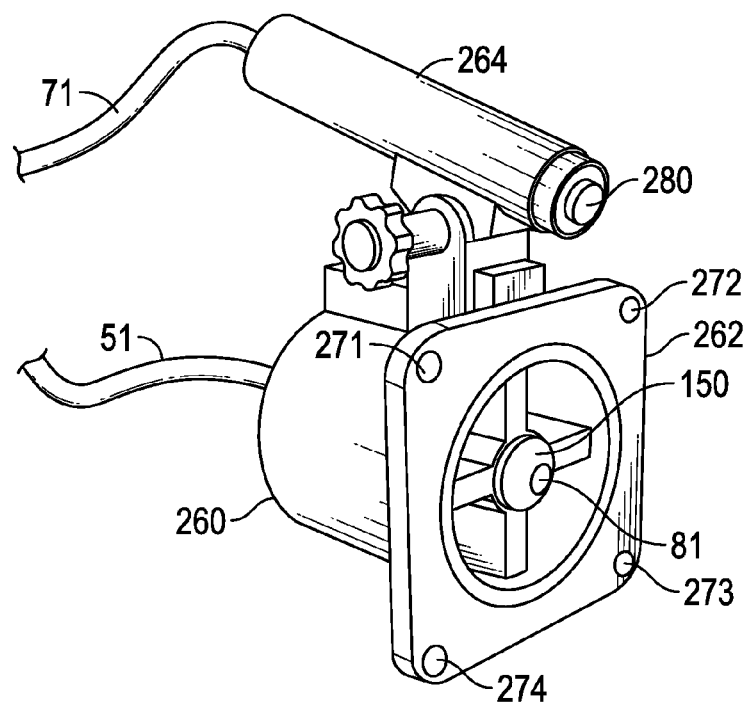
FIG. 6 is a perspective view of the left hand optical treatment head and housing with sensor attached, of FIG. 1.

FIG. 6 illustrates a perspective view of the right hand optical collection device 158 in housing 264 with optical collection node 83 encased by head unit 280. Housing unit 264 is attached to casing unit 260 which envelopes the right hand optical treatment device shown in FIGS. 5, 9, and 10. Mounting unit 262 is attached to the treatment end of casing unit 260. Mounting unit 262 is fitted in each corner with holes 271-274 such that another plate is affixed to the unit with a screw and nut, or like method.

FIGS. 1 and 13-18, illustrate several embodiments of a bilateral system for discontinuous/adjustable/patterned photochemical ocular treatment such as corneal and/or scleral collagen cross-linking using riboflavin as a photosensitizer. In those embodiments, UVA/blue light is used for the excitation energy. Referring to FIGS. 1 and 2, an illumination source unit 10 contains a multi-spectral light source 11 that delivers a user-selected excitation wavelength to bifurcated, UV transmissive liquid light guide 18. The light guide splits into separate light guide outputs 21 and 22 that are connected to illumination intensity adjustment module 30 mounted on a mobile pole stand comprised of pole 25 mounted on a base 23 with casters. Other support stands of different configuration are used in place of pole 25 with base 23 in alternative embodiments. Outputs of module 30 are connected by light guides 50, 51 to respective left and right optical treatment devices or units 150, 151. As described in detail above, the ophthalmic treatment system also includes monitoring system 40 for the photoluminescence emitted from the riboflavin interaction with UVA/blue light, using optical collection device 158 as illustrated in FIG. 9, and shown encased in housing unit 264 in FIG. 6. The left treatment device 260 is described in more detail below in connection with FIGS. 13 to 18. The right treatment device 261 is identical to the left treatment device 260.

Figure 13:
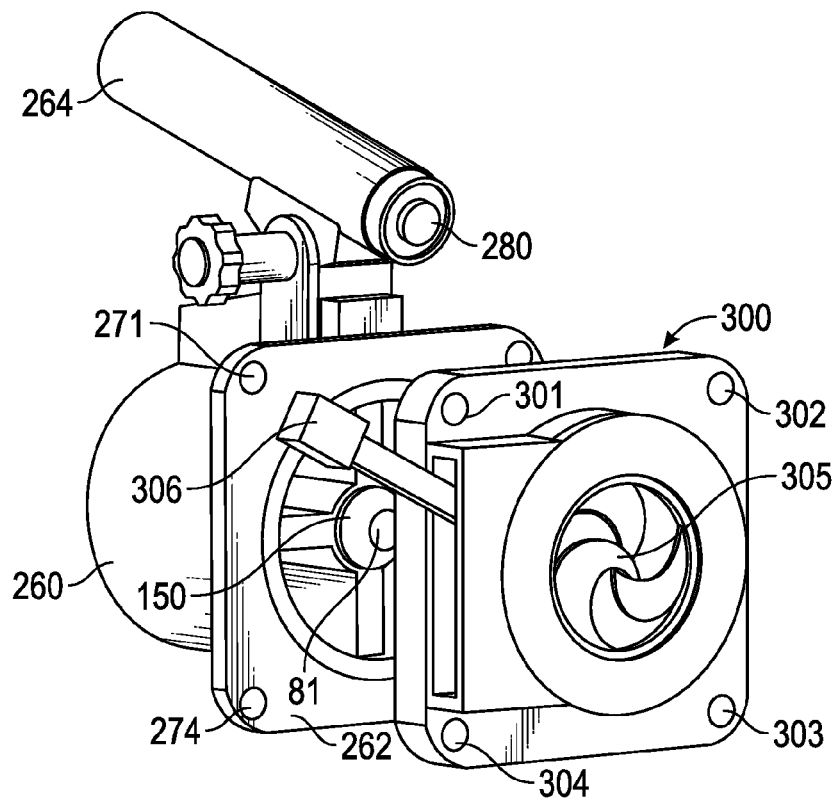
FIG. 13 is a perspective view of one embodiment of a corneal and/or scleral treatment head with sensor device and manually operated mechanical light modulating device (for example, a shutter and/or filter)
Figure 14:
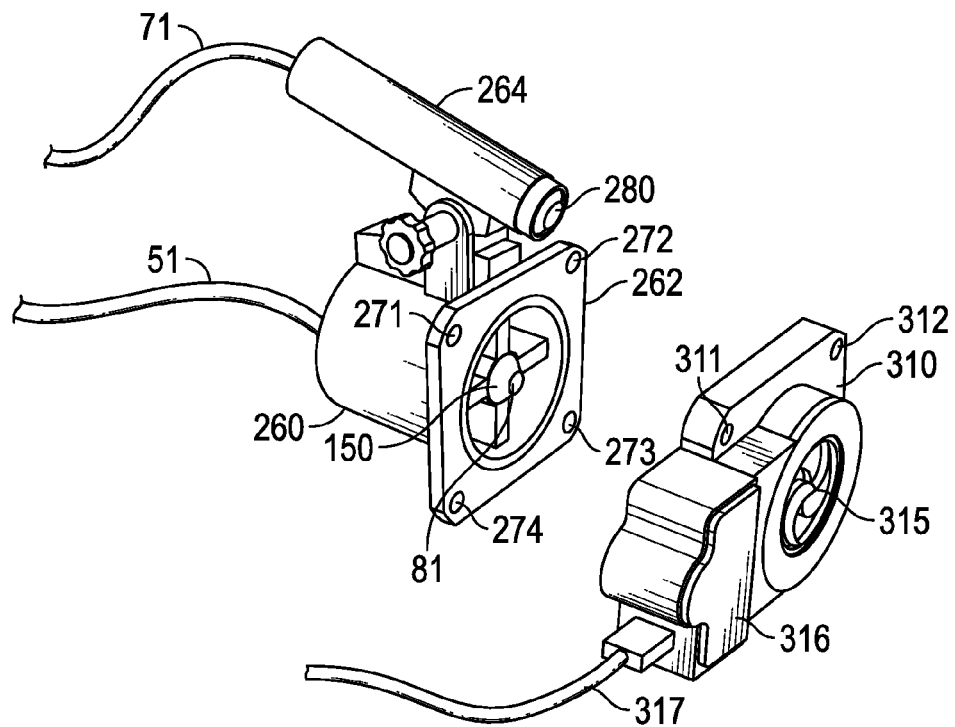
FIG. 14 is a perspective view of one embodiment of a corneal and/or scleral treatment head with sensor device and microprocessor-controlled mechanical light modulating device (for example, a shutter and/or filter) attached.

FIG. 13 illustrates a manually operated mechanical light modulating device (for example, a shutter and/or filter) housed in mounting unit 300 which is affixed to treatment mounting unit 262 at points 271-274, with a screw and nut, or like method, through points 301-304. When lever 306 is moved to the down position, mechanical light modulating device (for example, a shutter and/or filter) 305 will open, allowing UVA/blue light from treatment head 81 to pass unobstructed onto the treatment area. Mechanical light modulating device (for example, a shutter and/or filter) 305 remains open until the treating physician deems it necessary to provide a period of discontinued light projection. The determination is assisted by data from optical collection device 264 mounted to treatment head casing 260, and connected to monitoring system 40, FIG. 1. Light collection guide 71 is not shown in this view for purposes of clarity but the receptacle for this light guide connects to the rear end of optical collection device 264. The mechanical light modulating device (for example, a shutter and/or filter) remains open for a period of photochemical crosslinking lasting 15 seconds to 10 minutes. Lever 306 is then moved to the up position, closing mechanical light modulating device (for example, a shutter and/or filter) 305. When mechanical light modulating device (for example, a shutter and/or filter) 305 is closed, no UVA/blue light from optical treatment head 81 will reach the treatment area. The mechanical light modulating device (for example, a shutter and/or filter) remains closed for a period of 15 seconds to 10 minutes in some embodiments to allow for tissue reoxygenation. The process of opening and closing mechanical light modulating device (for example, a shutter and/or filter) continues as many times as the physician deems necessary.

FIG. 14 illustrates an automatic mechanical light modulating device (for example, a shutter and/or filter) housed in mounting unit 310 which is affixed to treatment mounting unit 262 at points 271-274, with a screw and nut, or like method, through points 311-314 (313 and 314 not shown). Automatic control unit 316 is affixed to mounting unit 310, and connected by cable 317 to UVA light source housing and control unit 10, FIGS. 1, 2. When treatment begins, mechanical light modulating device (for example, a shutter and/or filter) 315 is opened by control unit 316, allowing UVA light from treatment head 81 to pass unobstructed onto the treatment area. The mechanical light modulating device (for example, a shutter and/or filter) 315 remains open for a treatment session of 15 seconds to 10 minutes, off-set by periods of discontinuous illumination lasting 15 seconds to 10 minutes. When mechanical light modulating device (for example, a shutter and/or filter) 315 is closed, no UVA/blue light from optical treatment head 81 reaches the treatment area. Duration of discontinuous illumination, and number of treatment cycles is set on display control unit 110, FIG. 3. In one embodiment, UVA or blue light may be provided in a fractionation cycle of 15 seconds ON/15 seconds OFF, and in this case the shutter is opened and closed automatically.

In another embodiment, automatic control unit 316 affixed to mounting unit 310 is connected by cable 317 to optical collection monitoring system 40, FIG. 1, 11. When treatment begins, mechanical light modulating device (for example, a shutter and/or filter) 315 is opened by control unit 316, allowing UVA light from treatment head 81 to pass unobstructed onto the treatment area. The mechanical light modulating device (for example, a shutter and/or filter) remains open until a microprocessor housed in monitoring system 40 (not shown), determines singlet oxygen levels are sufficiently depleted. Light modulating device (for example, a shutter and/or filter) 315 is then automatically closed, allowing no UVA/blue light from optical treatment head 81 to reach the treatment area. Light modulating device (for example, a shutter and/or filter) 315 remains closed for a period of time lasting 15 seconds to 10 minutes. This process is repeated until treatment is complete.

Figure 15:
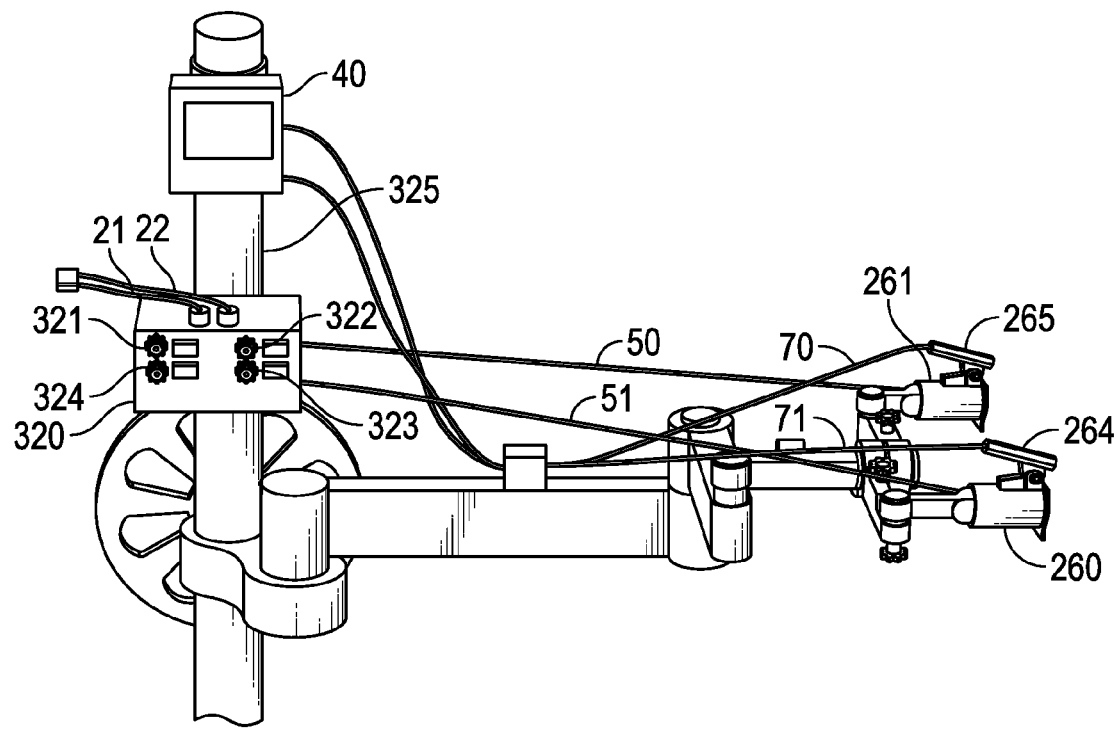
FIG. 15 is a perspective view of one embodiment of a corneal and/or scleral treatment head with sensor device attached, and microprocessor-controlled dimmer switch attached to the light source and sensor device.

FIG. 15 illustrates a manually or automatically controlled dimmer unit 320 mounted on a mobile pole stand comprised of pole 25 mounted on a base 23 with casters. Other support stands of different configuration are used in place of pole 25 with base 23 in alternative embodiments. During treatment, dials 321-324 are turned manually to increase or decrease the intensity of the UVA/blue light administered to the treatment areas. When treatment begins, gradually increasing from 0% to 100% intensity will mitigate the startling effect. The UVA/blue light remains at 100% intensity until the administering physician deems it necessary to provide a period of discontinued UVA/blue light projection. This determination is assisted by data from optical collection device 264 mounted to treatment head casing 260, and connected to monitoring system 40. The UVA/blue light remains at 100% intensity for a period of time lasting 15 seconds to 10 minutes. Knobs 321-324 are then engaged to gradually decrease the intensity of the UVA/blue light from 100% to at or near 0%, in order to mitigate the startling effect. At or near 0% intensity, little or no UVA/blue light from optical treatment heads reaches the treatment areas. The intensity remains at or near 0% for a period of 15 seconds to 10 minutes to allow for tissue reoxygenation. The process of increasing and decreasing the intensity continues as many times as the physician deems necessary.

In another embodiment, intensity is increased and decreased automatically by a microprocessor-controlled dimmer switch housed in dimmer unit 320 (not shown). The microprocessor controlled dimmer switch is connected by cable 325 to UVA light source housing and control unit 10, FIGS. 1,2. When treatment begins, light intensity is gradually increased to 100% allowing UVA light from treatment head 81 to pass un-dimmed onto the treatment area. The light remains un-dimmed for a treatment session lasting 15 seconds to 10 minutes, off-set by period of discontinuous illumination wherein the light is slowly reduced in intensity from 100% to at or near 0%. Light intensity remains at or near 0% for 15 seconds to 10 minutes. When light intensity is at or near 0%, no or little UVA/blue light from optical treatment head reaches the treatment area. Duration of discontinuous illumination, and number of treatment cycles are set on display control unit 110, FIG. 3.

In another embodiment, during treatment, intensity is increased and decreased automatically by a microprocessor-controlled dimmer switch housed in dimmer unit 320 (not shown). The microprocessor-controlled dimmer switch is connected by cable 325 to optical collection and monitoring system 40. When treatment begins, UVA/blue light automatically increases intensity from at or near 0% to 100%. The light intensity remains at 100% until a microprocessor housed in optical monitoring system 40 (not shown), determines singlet oxygen levels are sufficiently depleted. Dimmer unit 320 then automatically reduces UVA/blue light intensity from 100% to at or near 0%, allowing no UVA/blue light from optical treatment heads to reach the treatment area. Light intensity remains at or near 0% for a period of time lasting 15 seconds to 10 minutes. This process is repeated until treatment is complete.

Figure 16:
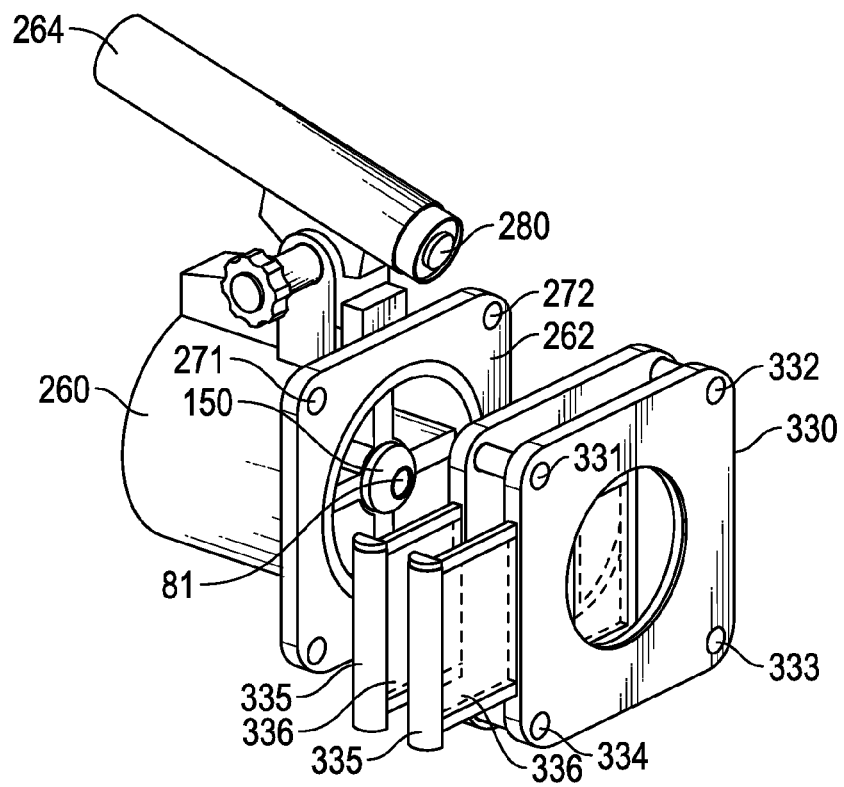
FIG. 16 is a perspective view of one embodiment of a corneal and/or scleral treatment head with sensor device and manually operated filter systems attached.

FIG. 16 illustrates a manually operated UVA/blue light filter housed in mounting unit 330 which is affixed to treatment mounting unit 262 at points 271-274, with a screw and nut, or like method through points 331-334. UVA filters 336 are held in place by housing units 335 which is slid into mounting unit 330 such that UVA filters 336 are directly in the path of the UVA/blue light emitted by treatment head 81. When slides 335 are removed from mounting unit 330, this allows UVA/blue light from treatment head 81 to pass unobstructed onto the treatment area. The slides remain free of the mounting unit until the treating physician deems it necessary to provide a period of discontinued light projection. This determination is assisted by data from optical collection device 264 which is mounted to treatment head casing 260, and connected to monitoring system 40, FIG. 1. Light collection guide 71 is not shown in this view for purposes of clarity but the receptacle for this light guide connects to the rear end of optical collection device 264. Slides 335 remain clear of mounting unit 330 for a period of time lasting 15 seconds to 10 minutes. Slides 335 are then inserted into mounting unit 330. When slides 335 are inserted into mounting unit 330, no UVA/blue light from optical treatment head reaches the treatment area. The slides remain in the mounting unit for a period of 15 seconds to 10 minutes to allow for tissue reoxygenation. The process of inserting and removing the slides continues as many times as the physician deems necessary.

Figure 17:
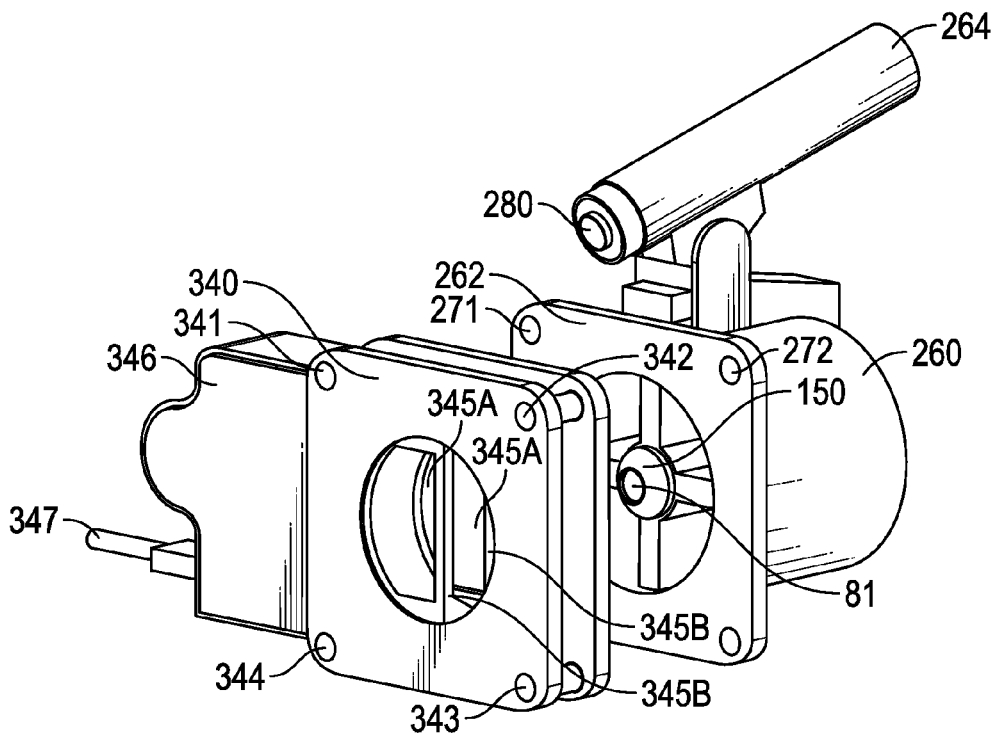
FIG. 17 is a perspective view of one embodiment of a corneal and/or scleral treatment head with sensor device and automatically operated filter system attached to microprocessor and sensor device.

FIG. 17 illustrates an automatically operated UVA/blue light filter housed in mounting unit 340 which is affixed to treatment mounting unit 262 at points 271-274, with a screw and nut, or like method, through points 341-344. Automatic control unit 346 is affixed to mounting unit 340, and connected by cable 347 to optical collection monitoring system 40, FIG. 1, 11, 15. UVA/blue light filters 345A are housed in retractable units 345B controlled by unit 346. When treatment begins, slides 345B are retracted, allowing UVA/blue light from treatment head 81 to pass unobstructed onto the treatment area. Filters 345B remain retracted until a microprocessor housed in monitoring system 40 (not shown), determines singlet oxygen levels are sufficiently depleted. Automatic control unit 346 then slides filters 345B into the path of light emitted from treatment head 81. When UVA/blue light filters are in the path of the UVA/blue light emitted from treatment head 81, no UVA/blue light reaches the treatment area. Filters 345B remain in the path of the light emitted from treatment head 81 for a period of 15 seconds to 10 minutes. This process is repeated until treatment is complete.

In another embodiment, an automatically operated UVA/blue light filter unit housed in mounting unit 340 is affixed to treatment mounting unit 262. Automatic control unit 346 is affixed to mounting unit 340, and connected by cable 347 to UVA light source housing and control unit 10, FIGS. 1,2. When treatment begins, slides 345B are retracted, by control unit 346 allowing UVA light from treatment head 81 to pass unobstructed onto the treatment area. The slides remain retracted for a treatment period of 15 seconds to 10 minutes, off-set by periods of discontinuous illumination where the slides are engaged, lasting 15 seconds to 10 minutes. When UVA/blue light filters 345A are obstructing the path of light emanating from treatment head 81, no UVA/blue light reaches the treatment area. Duration of discontinuous light projection, and number of treatment cycles is set on display control unit 110, FIG. 3

Figure 18:
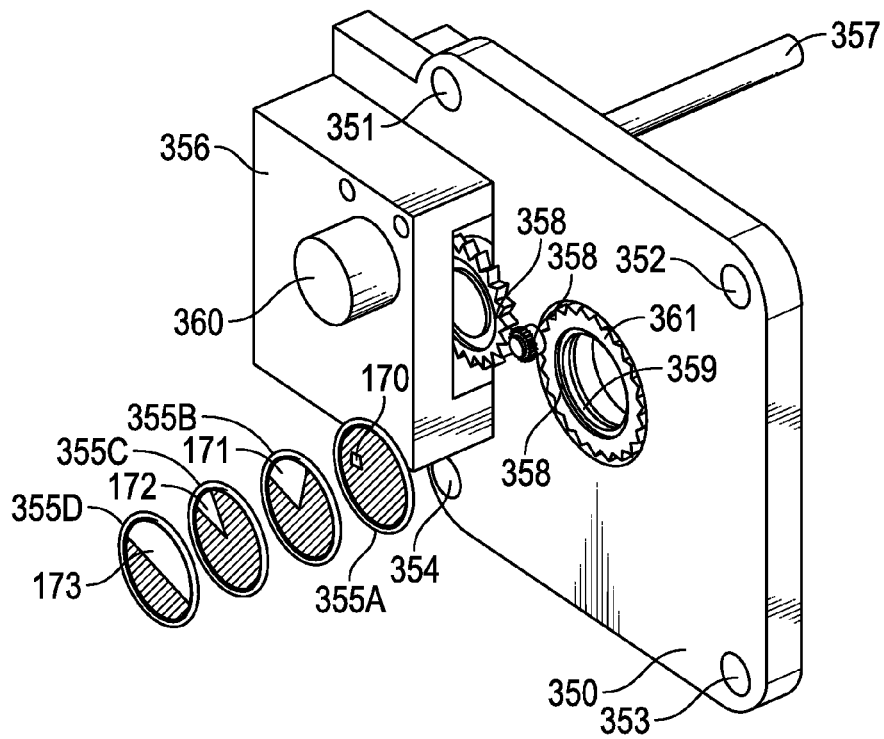
FIG. 18 is a perspective view of one embodiment of a rotating radiation pattern assembly which is attached to the corneal and/or scleral treatment head casing.

FIG. 18 illustrates a rotating UVA/blue light filter assembly, 350. Filter discs 355A, 355B, 355C, or 355D allow for variable treatment areas. Filter disc 355A has a UVA transparent spot 170 offset from the center of the disc, filter disc 355B has a UVA transparent region 171 of around 90 degrees of the circular disc area with the rest of the disc being solid or black, filter disc 355C has a UVA transparent region 172 of about 30 degrees with the rest of the disc being solid, and filter disc 355D has a transparent region of 180 degrees with the rest of the disc being solid. Filter discs with other arrangements of UVA transparent and solid areas may be provided in other embodiments. Filter discs are housed in rotating disc assembly 359, held in place by pin 361, and rotated by gear assembly 358. Light filter assembly 350 is affixed to treatment mounting unit 262 at points 271-274 (not shown), with screw and nut, or like method, through points 351-354. Automatic control unit 356 is affixed to filter assembly 350, and connected by cable 357 to UVA light source housing unit 10, FIGS. 1, 2 (not shown). Before treatment begins, a treatment disc 355A, 355B, 355C, or 355D is inserted into housing unit 359. When treatment begins, disc is rotated in a circular motion. Selected disc allows UVA/blue light to pass through the transparent portion, and no UVA/blue light to pass through the solid portion. The period of time for disc to make one full rotation is a treatment cycle. Duration of treatment cycles is set on display control unit 110, FIG. 3. In the case of disc 355A, an annular treatment area is provided by one full rotation of the disc.

Figure 19:
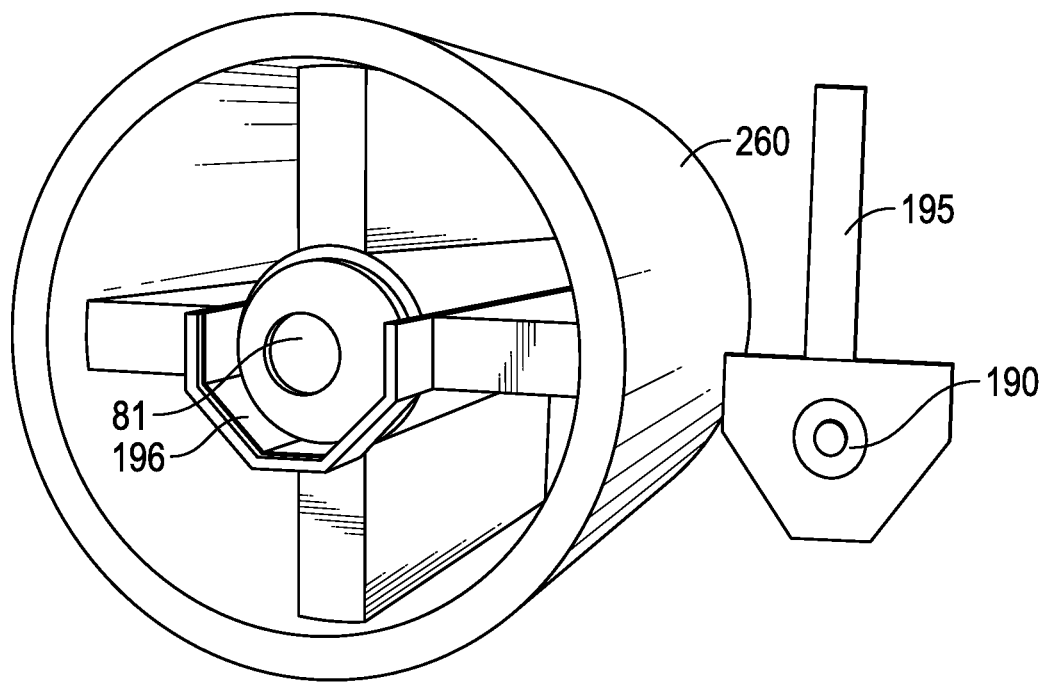
FIG. 19 is a perspective view of one embodiment of a filter with an aperture which allows for unequal doses of UVA/blue light to be applied to various portions of the treatment area.
Figure 20:
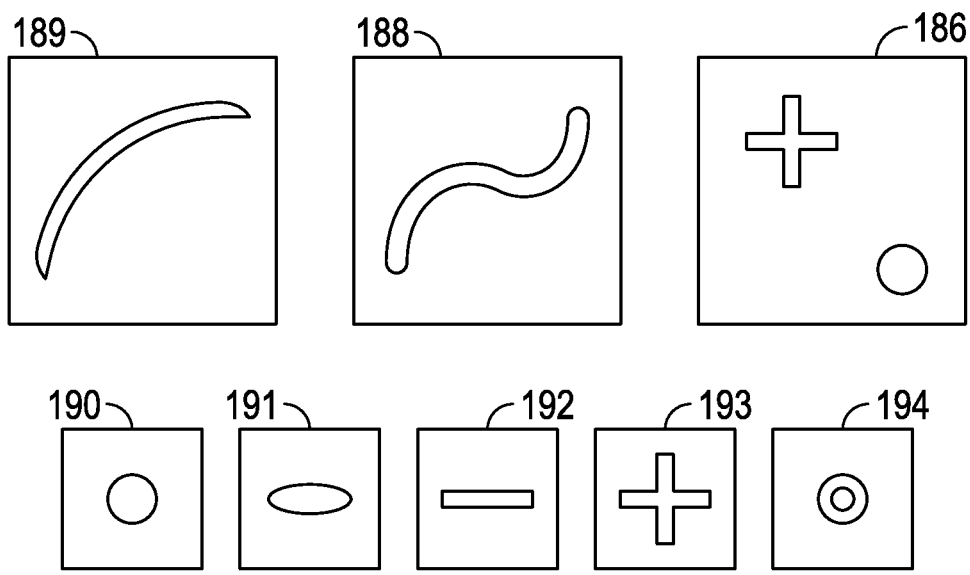
FIG. 20 illustrates one embodiment of a kit of optical masks or reticles with treatment light transmitting openings of various different patterns, shapes, and sizes.

FIG. 19 illustrates a perspective view of a UVA/blue light treatment head and casing with holder 196 for changeable irradiation pattern reticle or mask 190 with handle 195 for positioning purposes. FIG. 20 illustrates some examples of additional reticles or masks 186, 188, 189 and 191 to 194 which have apertures or windows of UVA and/or blue light transparent material providing a variety of different light distribution patterns and sizes desired by the physician, allowing more light to reach selected parts of the treatment area. For example, reticle 191 has an oval aperture, reticle 192 has a slit shaped aperture, reticle 193 has a square shaped aperture, reticle 194 has an annular ring shaped aperture, reticle 186 has two apertures of different shapes, reticle 188 has a pseudo tilde or "squiggly line" aperture, and reticle 189 has a crescent shaped aperture. The squiggly line aperture of reticle 188 may be thicker or wider in one segment, as illustrated, or may be of the same proportions throughout. As illustrated in reticle or mask 186, two or more apertures of the same or different shapes may be provided where different areas of the eye are to be treated simultaneously. Additional masks with apertures or patterns of apertures of different shapes and sizes may also be provided in a patterned mask kit, to provide expanded custom treatment options.

Although the mask 190 is positioned in holder 196 by hand in the embodiment of FIG. 19, alternative embodiments may have an automatic control unit affixed to housing 260, and connected by cable to a controller or microprocessor. The reticles or masks of different aperture sizes and shapes are housed in retractable units controlled by the automatic control unit. When treatment begins, the operator selects a pattern at an input device (for example as described below in connection with the embodiment of FIGS. 23 to 28) and the automatic control unit slides the selected reticle or mask into the path of light emitted from treatment head 81. This may be used in conjunction with a shutter for discontinuous treatment as described above.

Figure 21:
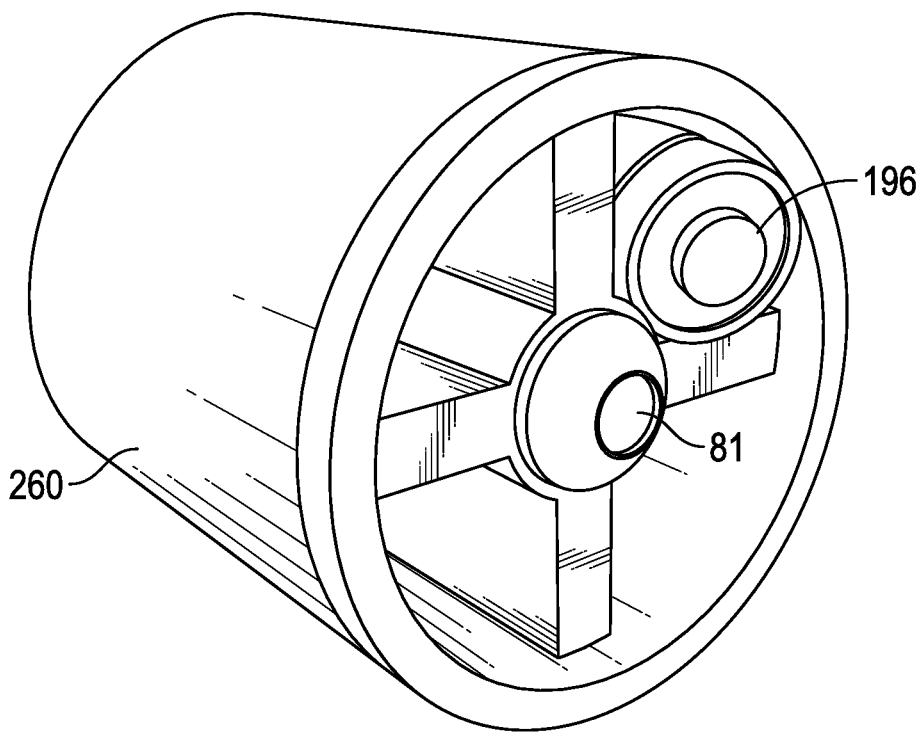
FIG. 21 is a perspective view of one embodiment of an additional light source utilized to reduce the startling effect by mitigating dramatic changes in light intensity or color seen by the patient.

FIG. 21 illustrates a perspective view of a UVA/blue light treatment head and casing 260 with a secondary non-treatment light source or anti-startle light source 196. In some embodiments, the secondary light source is powered on in such a way as to mitigate dramatic changes in light seen by the patient as the UVA/blue light is filtered, blocked, or dimmed. The secondary light source is of a wavelength and intensity fitting to reduce the startling effect a patient experiences as a result of dramatic changes in light intensity or color. In one embodiment, light source 196 is a green LED light. The secondary light source may be affixed to the treatment head casing in such a way that it is visible by the patient during periods of discontinuous illumination.

Figure 22:
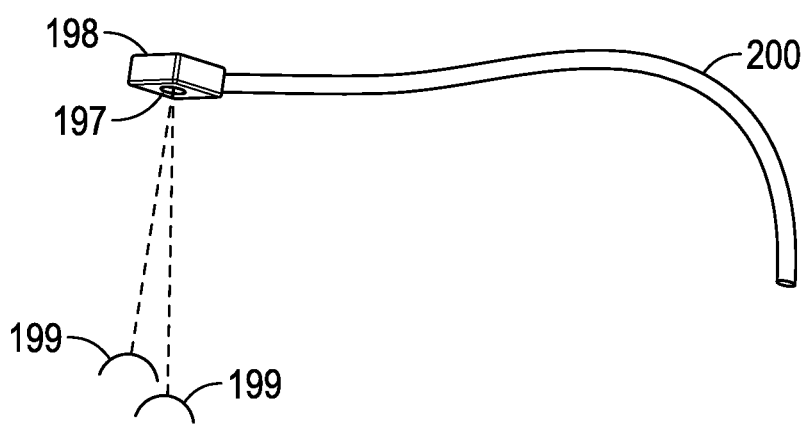
FIG. 22 is a perspective view of one embodiment of a fixation light.
Figure 23:
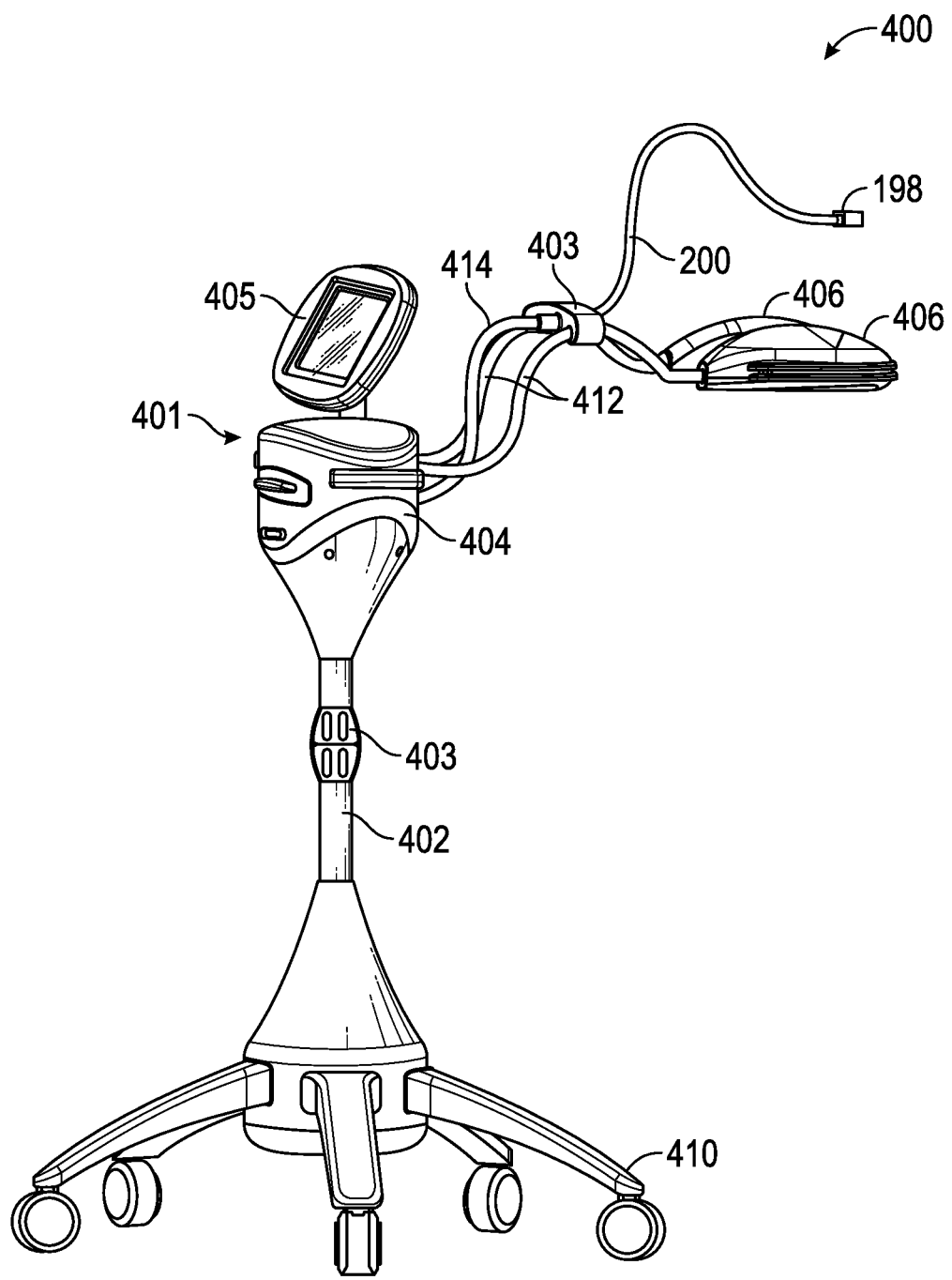
FIG. 23 is a front perspective view of another embodiment of an ophthalmic treatment system or device for corneal and/or scleral treatment.
Figure 24:
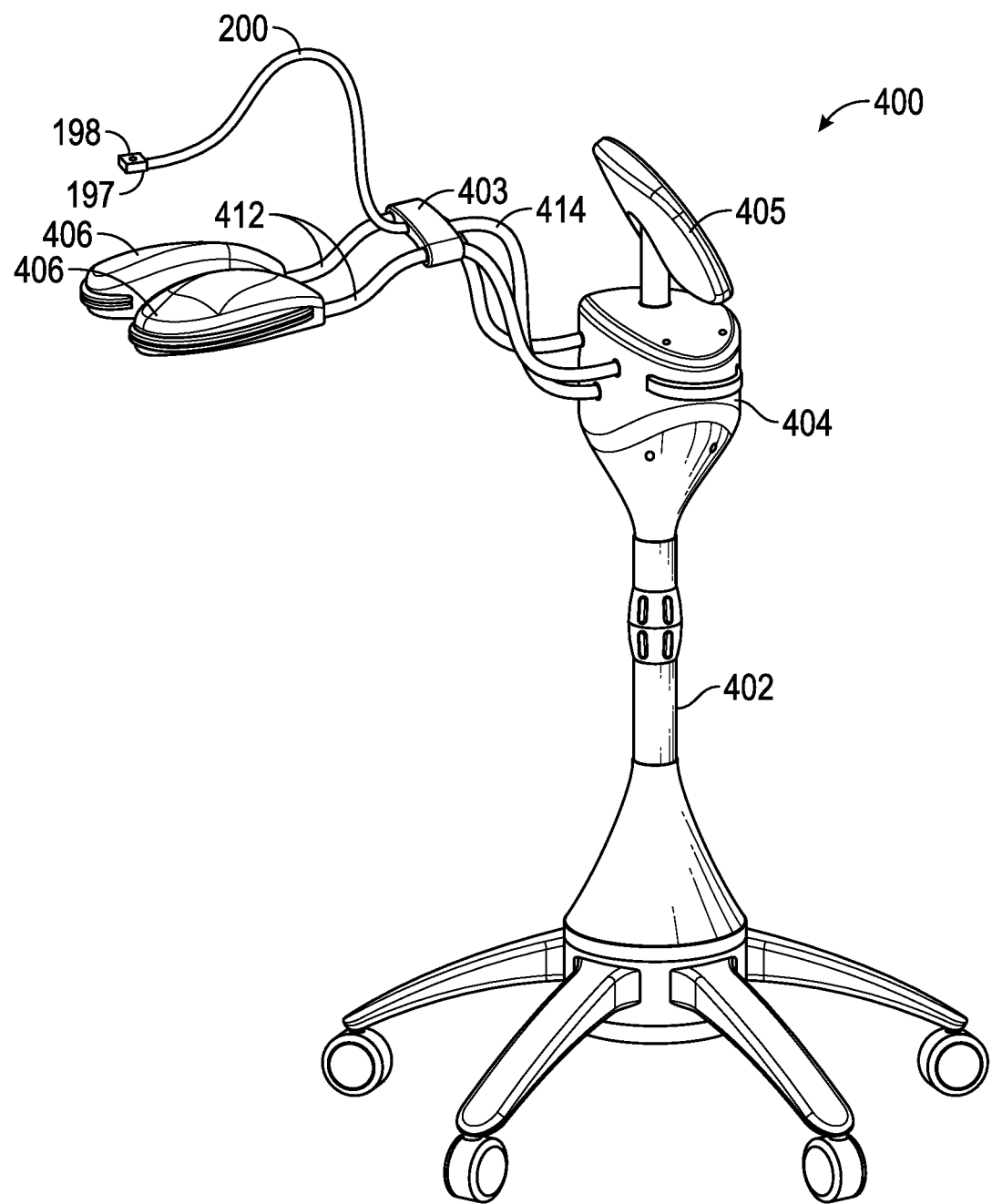
FIG. 24 is a rear perspective view of the ophthalmic treatment system of FIG. 23.

FIG. 22 illustrates one embodiment of a fixation light 197 in housing 198 attached to a supporting arm or gooseneck 200 which can be manually adjusted so that the fixation light is positioned over the patient's eyes 199 at a distance of 10 to 24 inches or greater, and serve as a focus point in order to maintain a stable treatment area. Fixation light may be controlled by a controller or microprocessor via cables extending through arm 200 to the light. The fixation light is a red light or any other light in the visible spectrum. The fixation light also performs a periodic blink or auditory cue to remind the patient to focus their attention on the fixation point in some embodiments. In another embodiment, each treatment head has its own separate fixation light.

FIGS. 23 to 30 illustrate an ophthalmic treatment device or system 400 according to another embodiment in which various control parameters are controlled remotely by the operator or physician via a computer input device, touch screen or the like, or are carried out automatically on entry of patient eye parameters by the physician. Treatment device 400 includes a control unit 401 mounted on a support stand having a wheeled base 410 and a telescoping pole 402 extending upwardly from the base and adjustable via rotatable telescoping pole lock 403 at a desired height. The control unit 401 comprises an enlarged housing 404 at the top of pole 402 and a touch screen user interface unit 405 mounted on top of housing 404. Treatment heads 406 are supported on respective flexible cable arms or goosenecks 412 extending from housing 404 and components within heads 406 are linked to control unit 401 via a wireless connection or wired connection through arms or goosenecks 412, as described in more detail below in connection with FIGS. 27 to 30. Fixation light 198 of FIG. 22 is also supported on stand 402 via gooseneck 200 extending from cable junction 403 and adjustable cable arm 414 extending from junction 403 to control unit 401.

Figure 26:
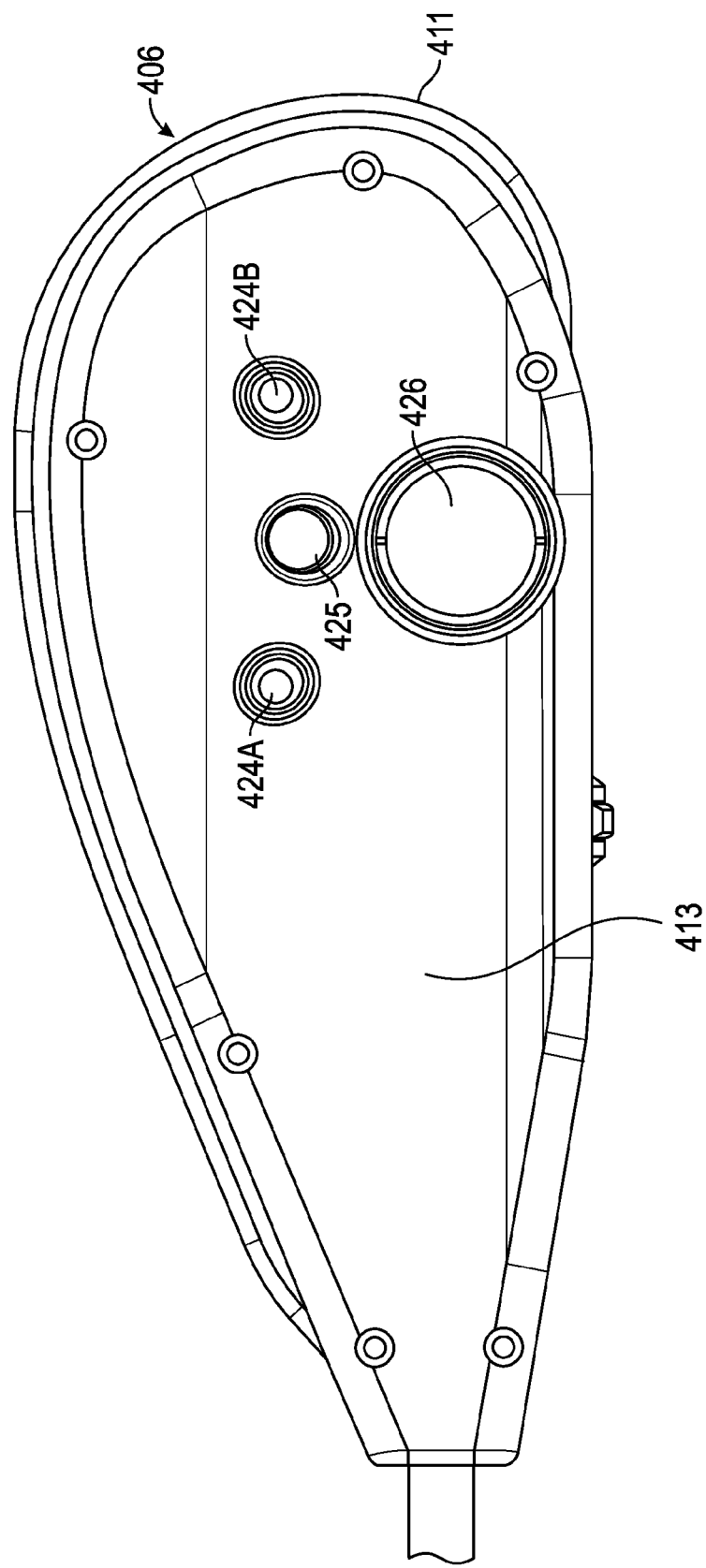
FIG. 26 is bottom plan view of one of the treatment heads of FIGS. 23 and 24.
Figure 27:
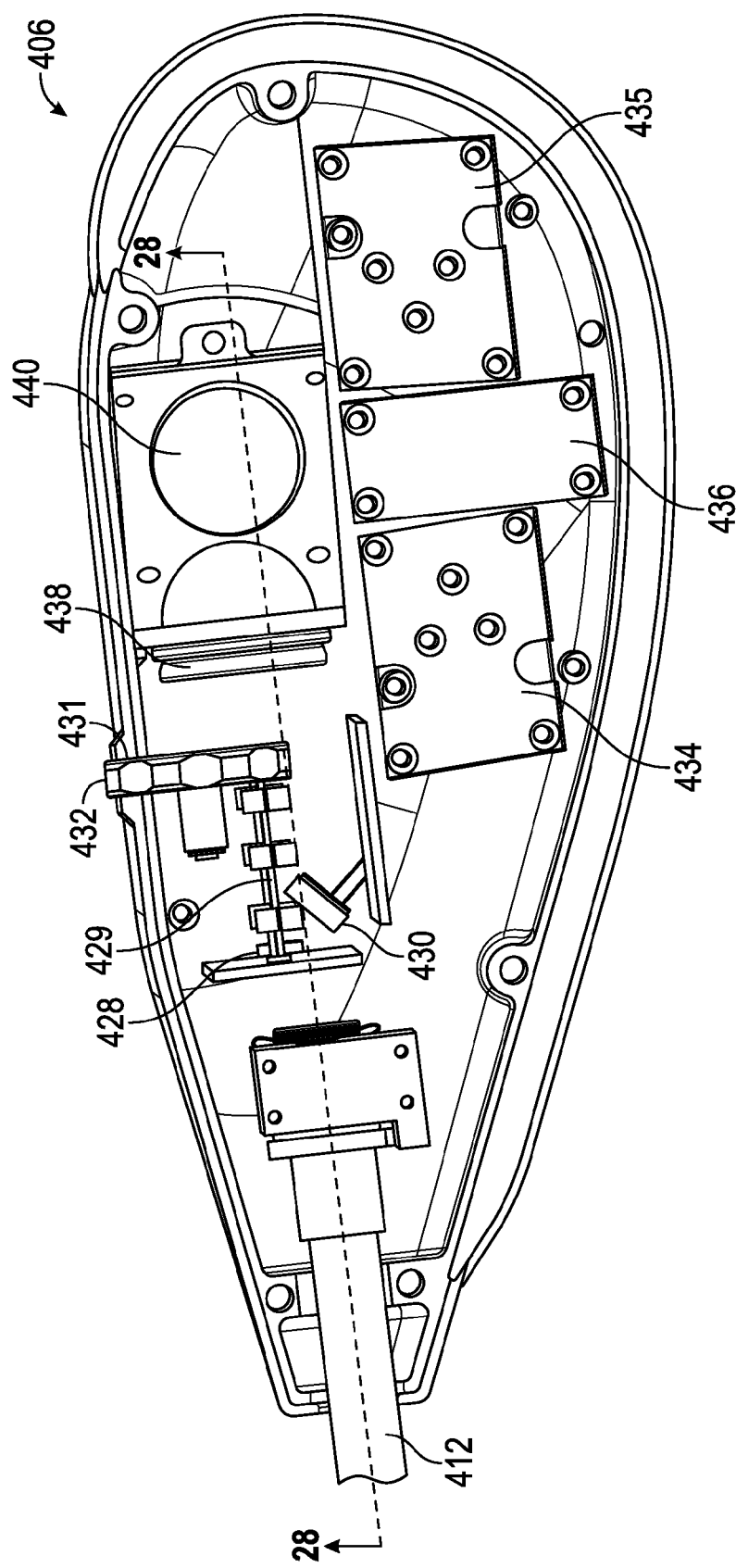
FIG. 27 is a view similar to FIG. 26 with the lower wall of the treatment head housing removed to reveal the internal system components.

As best illustrated in FIGS. 26 to 28, in one embodiment each treatment head 406 comprises a generally elongate outer housing 411 secured to gooseneck 412 at one end and having a lower, generally flat wall 413 in which a large UVA/blue light output port 426 is located, along with two adjustment or positioning light output ports 424A and 424B for adjustment or positioning light, and a photoluminescence monitor input port 425 (see FIG. 26). As illustrated in FIGS. 27 and 28, one side of the housing contains the optical system or light path from UVA and/or blue light emitter or LED 428 to the UVA/blue light output port 426. The other side of the housing contains printed circuit boards 434 and 435 carrying red and green light adjustment LEDs directed to respective red and green light positioning output ports 424A and 424B, respectively, along with associated control circuitry. A third printed circuit board (PCB) 436 carries a photoluminescence sensor or monitor 436 (FIG. 30) which receives input from input port 425. The output from photoluminescence monitor 436 is communicated via leads in arm 412 to the controller or microprocessor 418 in the control housing 404 at the upper end of stand 400.

Figure 25:
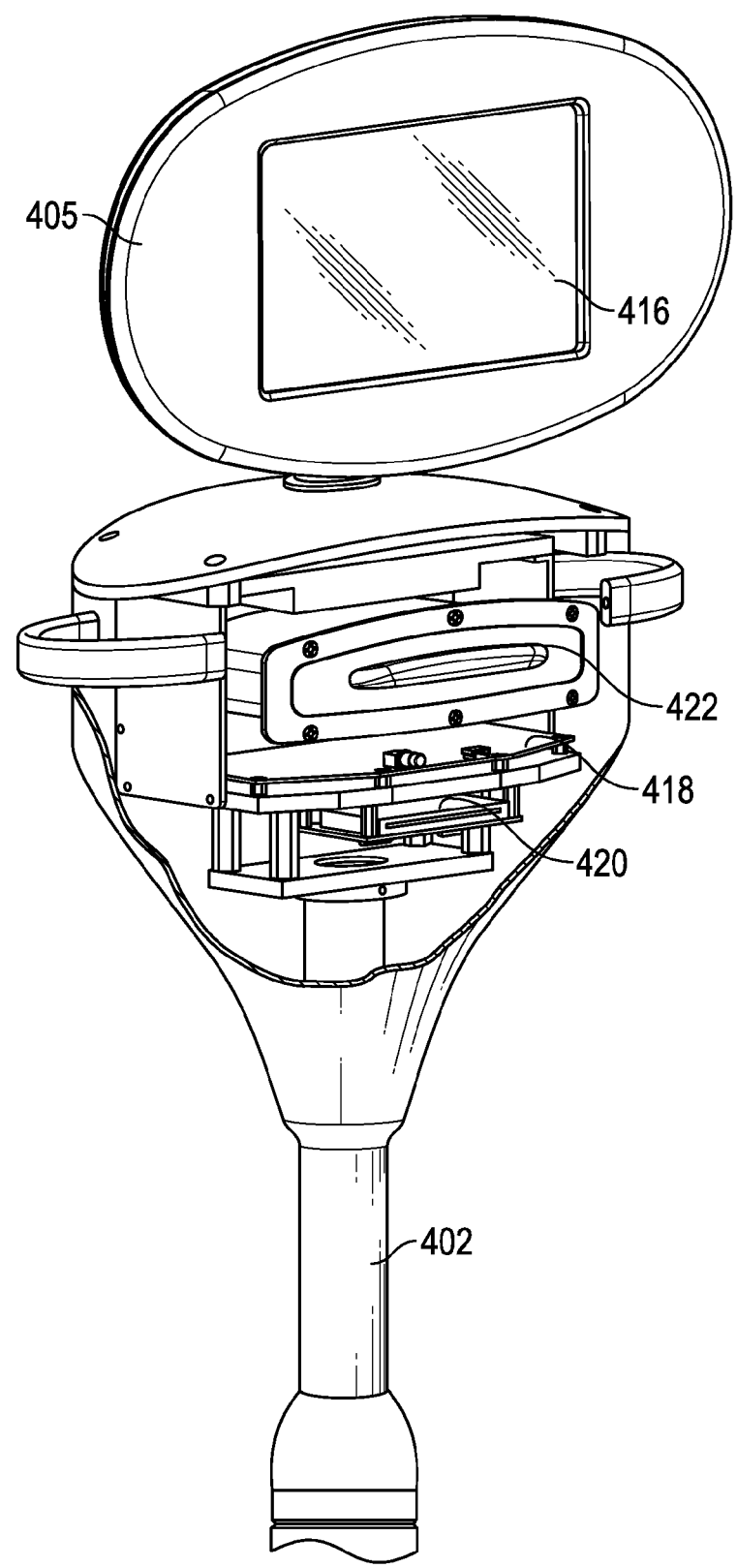
FIG. 25 is a perspective view of the control system housing and touch screen user interface of FIGS. 23 and 24, with the front wall of the control system housing broken away to reveal internal parts of the system.

As illustrated in FIGS. 27 and 28, the UVA or UVA/blue light source 428 has an output directed through light homogenizer or light guide 429 along a light path through lens 438 to 90 degree mirror 440, which directs the light downward through output port 426 of FIG. 26. A mask or reticle wheel 432 is rotationally mounted on shaft 433 in the light path. As illustrated in FIG. 29, reticle wheel 432 has a series of openings of different diameter around its periphery. Part of the periphery of wheel 432 extends out through a slot 431 in housing to allow the wheel to be turned manually in order to align a selected opening with the UVA or UVA blue light path. In one embodiment, the openings in the pupil or reticle wheel allow adjustment of the beam spot size in the range from around 9 to 12 mm. In an alternative embodiment, a drive motor, stepper, or external gear wheel (as in FIG. 18) may be provided for moving wheel 432 according to a user input at user interface 416, which may be a touch screen as illustrated in FIG. 25 or a keypad. Additionally, a plurality of reticle wheels with openings of different sizes and shapes, such as the shapes shown in FIG. 20 and other alternative shapes, may be provided for selective placement in the light path in place of wheel 432. The reticle wheel may be replaced manually or automatically under the control of microprocessor 418, for example as described above in connection with FIGS. 17 and 18. Thus, beam size and shape may be modified in order to produce a selected size and pattern of the treatment light projection onto an eye.

Although the treatment LED or light source in this embodiment is a single LED, an array of multiple light sources or LEDs, e.g. two or more LEDs, may be provided as the UVA, blue or UVA/blue light source in alternative embodiments. As illustrated in FIG. 28, an anti-startle light source 450 is positioned in the housing directly above UVA LED 428, and light output from source 450 is directed via light guide or beam homogenizer 451 and lens 439 in a path parallel to the treatment light beam up to 90 degree mirror 441, which directs the anti-startle light beam downwards through output port 426. In one embodiment, the anti-startle light source is a green light LED but it may be a visible light of other colors in alternative embodiments.

In one embodiment, microprocessor 418 is programmed to turn the UVA or UVA/blue light source or LED on and off at predetermined intervals, to provide discontinuous UVA treatment light. The green anti startle LED 450 is turned on when the UVA treatment light is off, for the reasons stated above in connection with the embodiment of FIG. 21. In one embodiment, the ON and OFF periods for discontinuous UVA treatment may be 15 sec. ON, 15 sec. OFF, and the total treatment time may be of the order of 20 to 30 minutes, with an intensity or irradiance of 3-4 mW/cm$^2$. In one embodiment, the irradiance or intensity is gradually increased at the start of each ON period, and gradually dimmed at the end of each ON period down to 0.1 or 0.2 mW/cm$^2$, and is not completely turned off before it is replaced by the green anti-startle light. Using this system, a UVA light of wavelength from 350 to 400 nm or UVA/blue light of wavelength of from 365-420 nm for deeper cross-linking is used to deliver an irradiance of from 3 to 30 mW/cm2, in discontinuous cycles variable from 1 second to 1 minute or more, and through a selected reticle or pupil wheel with apertures that provide a specific light distribution pattern to cross-link selected areas of the cornea and/or sclera. However, all of these parameters (frequency and length of treatment light exposure periods, irradiance, total treatment time, beam size, beam shape) may be varied based on the particular treatment requirements, and some or all of the treatment parameters may also be varied automatically based on feedback to the microprocessor 418 from the photoluminescense monitoring device 436.

In this embodiment, X, Y and Z positioning of the treatment heads may be carried out manually by the operator or physician using the flexible goosenecks, with the assistance of the red and green positioning LEDs 424A and 424B for locating each head at the desired height above the eye and with the treatment beam aligned with the desired position on the eye. By providing two angled alignment beams of different colors, it is easier for the operator to determine when the treatment head is at the desired working distance from the eye with the UVA/blue light output port aligned with the desired treatment area, when the red and green aiming beams coincide with each other as a single yellow spot on the eye. In other embodiments, a robotic positioning system controlled by the microprocessor may be used to position the treatment heads.

In one embodiment, the UVA light source was a NCSU033B UV LED manufactured by Nichia Corporation of Tokushima, Japan, but other UVA LEDs with similar properties may be used in other embodiments. The green anti-startle LED, red and green positioning LEDs, and red fixation LED are selected to have flux densities well below the maximum safe or allowable flux onto the pupil of an eye. The green and red LEDs in one embodiment were parts LT T673 N1S1 25 Z (green LED) and LR T67F-U1AA-1-1 manufactured by Osram GmbH of Munich, Germany, but other red and green LEDs with similar properties may be used in other embodiments.

Figure 30:
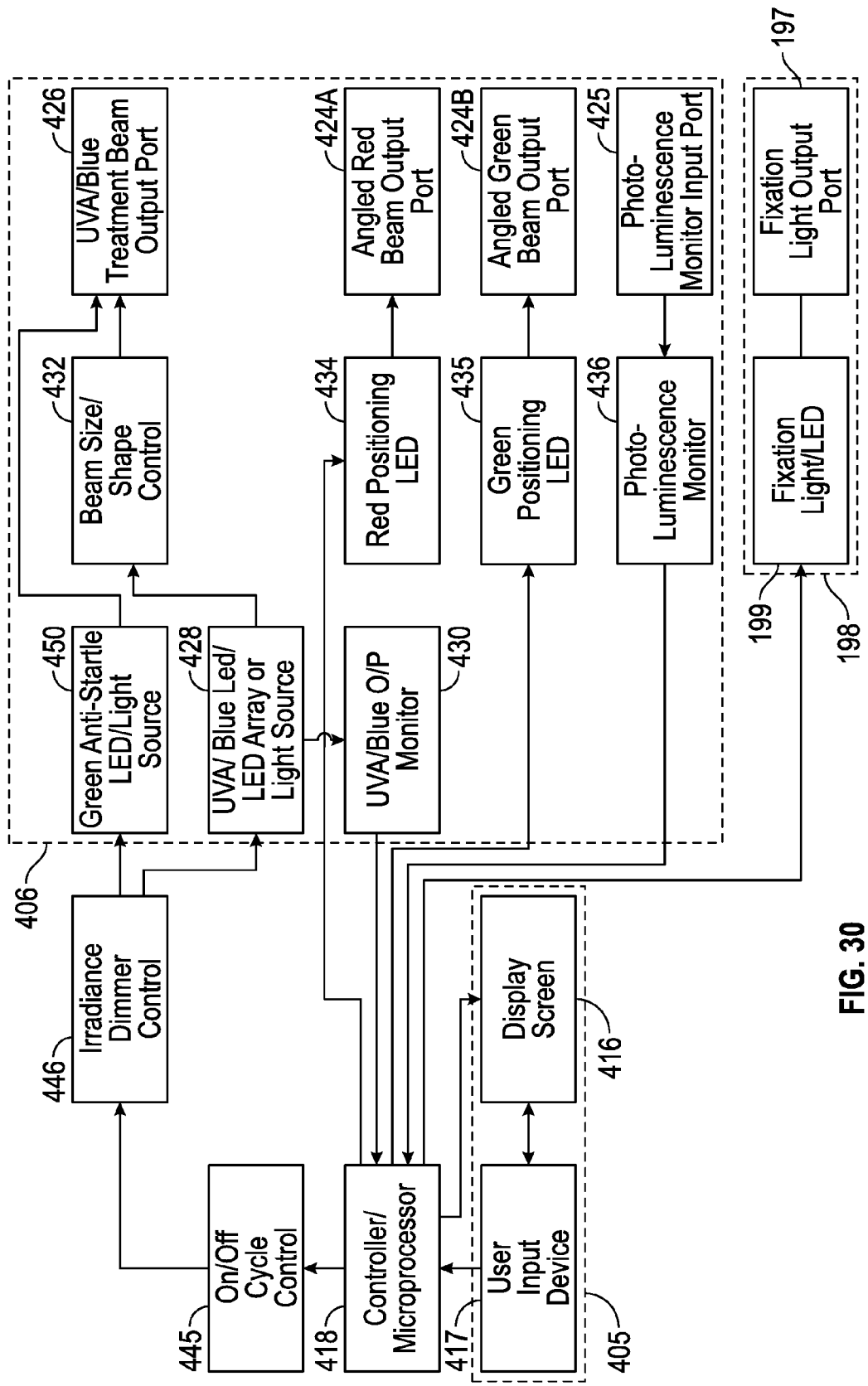
FIG. 30 is a block diagram of the system of FIGS. 23 to 29.

FIG. 30 is a block diagram of the control system for the treatment device of FIGS. 23 to 30. As illustrated, microprocessor 445 controls the on/off treatment cycle or discontinuous irradiation 445 of the UVA or UVA/Blue light source or light source array 428, and also controls turning on and off of the green anti-startle LED 450 so that it is ON when the UVA light is OFF. It should be understood that the UVA treatment LED is not necessarily turned off completely during the treatment OFF periods, but may be turned down to a minimal irradiance or intensity during these periods. The system also includes an irradiance or dimmer control 446 which controls irradiance level based on input from controller 418 in response to programmed instructions or input from the operator. UVA/blue output sensor or monitor 430 detects irradiance level and provides a feedback input to controller 418. The UV or UVA beam size and shape is controlled by selected reticles in pupil wheel or reticle holder 432 located between the UVA LED and the output port 426 as described above in connection with FIGS. 28 and 29, and selection of the appropriate size and shape opening for alignment with the LED output may be performed manually by the operator at the start of each treatment, or automatically via an input from microprocessor or controller 418.

The red and green positioning LEDs 424A and 424B are also controlled by microprocessor 418 and may be switched on by user input on the touch display screen, for example, when positioning the treatment heads. Once positioning is completed, the positioning LEDs are turned off. Output from the photoluminescence monitor 436 is also provided to microprocessor 418 and may be displayed on the display screen or touch screen 416 for use in determining various treatment parameters including amount of riboflavin solution to be added, variation of ON/Off treatment cycles, and the like. Fixation light or LED 199 is switched on at all times during treatment so that the patient can focus their eyes on the light and maintain a static or substantially static The systems and methods described above allow for bilateral or monocular photochemical cross-linking of corneal and/or scleral collagen employing selectable UVA/blue light as the excitation source and riboflavin as the photosensitizer. One embodiment of the system has an illumination source with multi-spectral capability, light guides for delivery of light to bilateral optical heads for projection onto the corneal and/or scleral surface of both eyes simultaneously, and in this system the light source is an Hg or Xe short arc lamp. The light source is connected to the treatment head or heads via liquid light guides, which produces improved homogeneity in the light beam. In another embodiment, the system has treatment heads each incorporating one or more treatment light sources and optics for directing a treatment beam from the light source out of an outlet port which may be positioned to direct the treatment beam onto a patient's eye. In this system, the light sources may be single wavelength or limited wavelength light sources such as LEDs or laser diodes.

The image projection optics are designed to produce a relatively large working distance between the treatment head and the eye, which is at least 50% greater than the working distance in prior art corneal treatment systems. This provides better visualization for the surgeon as well as better access for discontinuous or diffusion augmentation technique, described in detail above. In some embodiments, provision is made for an adjustable working distance.

In some or all of the foregoing embodiments, a highly oxygenated topical solution is placed on the cornea and/or sclera for stromal reoxygenation during cross-linking treatment, such as a solution containing iodide ion or a lipid or oil-based fluid that is pre-oxygenated at a high oxygen partial pressure. In another alternative, a hydrogen peroxide reducing agent or solution is applied to the eye which converts hydrogen peroxide produced in the stroma during irradiation of the eye into oxygen and water. Suitable reducing agents for application to the eye for this purpose are topical solutions containing iodide ion or the enzyme catalase. These agents are added to any standard riboflavin solution or as a separate solution applied to the cornea and/or sclera during photochemical treatment in some embodiments.

In some embodiments, the disclosed treatment system treats conditions including iatrogenic effect or the prevention of iatrogenic effect, from surgical intervention such as cataract surgery or corneal grafting, refractive intervention such as Laser-Assisted in Situ Keratomileusis (LASIK) or photorefractive keratectomy (PRK), radial keratotomy (RK), or prosthesis, corneal inlays or onlays, or medications, or the cause of corneal or scleral weakness can be congenital, idiopathic or due to microbial causes or trauma.

In some embodiments, the disclosed treatment system treats keratoconus, ectasia, Terrien's marginal degeneration, pellucid marginal degeneration, and corneal melting or ulcer, or normal or weakened corneas that require from 0.25 to 4.0 diopters or more of refractive correction for the treatment of myopia, hyperopia, astigmatism or other refractive errors of the eye, or corneal inflammatory disorders such as infectious *keratitis* and/or corneal ulcers.

A non-limiting example for using the ophthalmic treatment systems to treat a patient with keratoconus is provided as follows. After topical local anesthesia of the eye, a proprietary sponge (e.g. the sponge disclosed in U.S. Provisional Application No. 61/617,339, filed on Mar. 29, 2012) is used to gently wipe the surface of the eye to remove tears, mucous, lipids, and other macromolecules, and to mildly disrupt but not remove the epithelium. A surgical sponge is then placed over a selected portion or the entire surface of the cornea and/or sclera, onto which is a 0.1% or greater riboflavin solution is applied every 30-60 seconds for 5-30 minutes. During this time, periodic assessments using slit-lamp microscopy are used to assess the concentration and homogeneity of stromal saturation. Thereafter, a custom mask is applied to the surface of the cornea and/or sclera, thereby allowing for UVA or UVA and blue light irradiation of selected areas of the cornea and/or sclera. A UVA or UVA/blue light of wavelength of from 365-420 nm for deeper cross-linking is used to deliver an irradiance of from 3 to 30 mW/cm2, in discontinuous cycles variable from 1 second to 1 minute or more, and through a reticule with an apertures that provides a specific light distribution pattern to cross-link selected areas of the cornea and/or sclera.

While only certain embodiments have been set forth, alternative embodiments and various modifications will be apparent from the above descriptions to those skilled in the art. These and other alternatives are considered equivalents and within the spirit and scope of this disclosure. The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:
1. An ophthalmic treatment system, comprising:
   a light source device;
   at least one optical treatment head operatively coupled to the light source device and defining an optical axis, and providing at least one treatment light concentric to the optical axis, the treatment light being selected from the group consisting of UVA light, blue light, and a mixture of UVA and blue light;
   at least one processor associated with the light source device and programmed to control the treatment light to provide discontinuous treatment light projection onto an eye for a selected treatment time comprising successive treatment light exposure periods separated by non-treatment periods, wherein the treatment light exposure periods and non-treatment periods are of equal duration; and
   a photosensitizer for application to the eye to promote corneal cross-linking during UVA light exposure periods, the photosensitizer comprising a riboflavin solu- tion containing iodide ion wherein the treatment light exposure periods and non-treatment periods of are 15 seconds.

2. The system of claim 1, wherein the processor has an input for operator selection of parameters and duration for the successive treatment light exposure periods on the cornea and/or sclera.

3. The system of claim 1, wherein the treatment light has a wavelength in the range from 350 to 400 nm.

4. The system of claim 1, wherein the treatment light has a wavelength in the range from 365 to 420 nm.

5. The system of claim 1, wherein the at least one processor is programmed to control the treatment light intensity during each treatment light exposure period to increase the treatment light intensity gradually to a maximum treatment light intensity at the start of each treatment light exposure period and to dim the treatment light intensity from the maximum treatment light intensity to a low level prior to the end of each treatment light exposure period.

6. The system of claim 1, further comprising an anti-startle light of visible colored light, wherein the at least one processor is programmed to direct the anti-startle light towards an eye of a patient under treatment during non-treatment periods between treatment light exposure periods and to switch off the anti-startle light during treatment light exposure periods.

7. The system of claim 1, wherein the at least one optical treatment head comprises a light source array having one light source, or a plurality of light sources.

8. The system of claim 1, further comprising an optical projection device configured to direct the at least one treatment light onto a portion of an eye.

9. The system of claim 1, wherein the at least one processor is programmed to apply the at least one treatment light onto an eye in a predetermined pattern.

10. The system of claim 1, wherein the light control device applies the at least one treatment light to an eye in a plurality of predetermined patterns.

11. The system of claim 1, further comprising a light modulating device which partially or entirely blocks or unblocks the light source, wherein the at least one processor is programmed to control the light modulating device to block and unblock all or part of the light source to provide the discontinuous treatment light projection on the eye.

12. The system of claim 1, further comprising a pattern control device which provides patterned treatment light projection onto the eye.

13. The system of claim 12, wherein the pattern control device is part of a light mask.

14. The system of claim 1, further comprising an optical sensor device which provides sensor output data to the at least one processor, and the at least one processor is programmed to adjust the intensity of part or all of the light source according to sensor output data collected from the optical sensor device.

15. The system of claim 14, wherein the optical sensor device is an optical collection device.

16. The system of claim 14, wherein the sensor device comprises a photoluminescent monitoring module which measures the intensity of photoluminescent emissions from the eye.

17. The system of claim 1, further comprising an environmental monitoring module which monitors concentrations of photosensitizer, oxygen, or both in the eye.

18. The system of claim 1, further comprising a fixation light in the visible light spectrum upon which an eye is focused during treatment.

19. The system of claim 1, wherein the light source device comprises at least one single-wavelength light source.

20. The system of claim 1, wherein said at least one optical treatment head comprises first and second optical treatment heads each including projection optics and configured to project respective treatment light onto the right and left eyes at a working distance of from two to six inches from the optical treatment heads.

21. The system of claim 20, wherein the first optical treatment head and second optical treatment head are adjustably mounted for multi-directional adjustment of the position of the optical treatment head relative to the respective eyes.

22. The system of claim 20, further comprising an intensity adjustment module configured to independently adjust the intensity of the at least one treatment light projected by the first optical treatment head and second optical treatment head.

23. The system of claim 1, further comprising a positioning apparatus associated with the optical treatment head, the positioning device comprising first and second visible light sources of different colors which emit respective first and second visible light aiming beams of different colors at an angle to the optical axis of the optical treatment head which cross over one another on the optical axis at a predetermined working distance from the optical treatment head sufficient to allow access to the eye during treatment when the eye is positioned at the cross over position of the aiming beams.

* * * * *